(12) United States Patent
Fong et al.

(10) Patent No.: US 10,973,675 B2
(45) Date of Patent: *Apr. 13, 2021

(54) DEVICES AND METHODS FOR ANCHORING A SHEATH IN A TISSUE CAVITY

(71) Applicant: Savage Medical, Inc., Belmont, CA (US)

(72) Inventors: Kenton D. Fong, Belmont, CA (US); Jan Lee, Pasadena, CA (US); Jeffrey W. Etter, Hayward, CA (US)

(73) Assignee: SAVAGE MEDICAL, INC., Belmont, CA (US)

( * ) Notice: Subject to any disclaimer, the term of this patent is extended or adjusted under 35 U.S.C. 154(b) by 694 days.

This patent is subject to a terminal disclaimer.

(21) Appl. No.: 15/798,094

(22) Filed: Oct. 30, 2017

(65) Prior Publication Data

US 2018/0125699 A1 May 10, 2018

Related U.S. Application Data

(63) Continuation of application No. 15/266,976, filed on Sep. 15, 2016, now Pat. No. 9,827,135.

(Continued)

(51) Int. Cl.
| | | |
|---|---|---|
| *A61F 5/44* | (2006.01) | |
| *A61F 5/449* | (2006.01) | |
| *A61F 2/04* | (2013.01) | |

(52) U.S. Cl.
CPC ............ *A61F 5/4408* (2013.01); *A61F 5/449* (2013.01); *A61F 2002/045* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,470,707 A | * | 10/1923 | Bates | .................. A61B 17/1114 606/154 |
| 3,155,095 A | * | 11/1964 | Brown | .................. A61B 17/11 606/154 |

(Continued)

FOREIGN PATENT DOCUMENTS

| | | |
|---|---|---|
| JP | H10328190 A | 12/1998 |
| JP | 2002537026 A | 11/2002 |

(Continued)

OTHER PUBLICATIONS

Extended European Search Report issued in related European Patent Application No. 16847327.0 dated Jul. 12, 2019.

(Continued)

*Primary Examiner* — Guy K Townsend
(74) *Attorney, Agent, or Firm* — Venable LLP; Michele V. Frank

(57) ABSTRACT

According to some embodiments of the invention, an anchoring system includes a sleeve having an inner surface defining a first lumen, a first annular sealing mechanism disposed at a proximal end of the sleeve, and a second annular sealing mechanism disposed at a distal end of the sleeve. The anchoring system further includes a pressure tube in fluid connection with an outer surface of the sleeve, a sheath in mechanical connection with the sleeve, the sheath forming a second lumen, the second lumen being in fluid connection with the first lumen, and open-cell foam disposed on the outer surface of the sleeve. Application of negative pressure to the pressure tube causes a seal to form between the first and second annular sealing mechanisms and an inner surface of a tissue cavity. Application of negative pressure to the pressure tube also creates a frictional force that resists displacement of the sleeve.

24 Claims, 19 Drawing Sheets

Related U.S. Application Data

(60) Provisional application No. 62/283,877, filed on Sep. 15, 2015.

(56) References Cited

U.S. PATENT DOCUMENTS

| | | | | |
|---|---|---|---|---|
| 3,620,218 | A * | 11/1971 | Schmitt | C08L 67/04 606/154 |
| 4,190,909 | A * | 3/1980 | Ablaza | A61F 2/06 623/1.32 |
| 4,627,837 | A | 12/1986 | Gonzalo | |
| 4,641,653 | A * | 2/1987 | Rockey | A61F 5/00 604/909 |
| 4,716,900 | A | 1/1988 | Ravo et al. | |
| 4,719,916 | A | 1/1988 | Ravo | |
| 4,721,109 | A * | 1/1988 | Healey | A61B 17/11 606/156 |
| 4,905,693 | A * | 3/1990 | Ravo | A61B 17/1114 606/153 |
| 5,151,105 | A * | 9/1992 | Kwan-Gett | A61F 2/06 604/103.05 |
| 5,156,620 | A * | 10/1992 | Pigott | A61F 2/82 604/916 |
| 5,180,392 | A * | 1/1993 | Skeie | A61B 17/1114 606/155 |
| 5,306,300 | A * | 4/1994 | Berry | A61F 5/0076 604/909 |
| 5,425,739 | A * | 6/1995 | Jessen | A61B 17/11 606/153 |
| 5,476,506 | A * | 12/1995 | Lunn | A61F 2/06 623/1.13 |
| D369,857 | S * | 5/1996 | Booth | A61B 17/11 D24/112 |
| 5,594,038 | A | 1/1997 | Kobayashi et al. | |
| 5,725,547 | A * | 3/1998 | Chuter | A61F 2/07 606/191 |
| 6,273,917 | B1 * | 8/2001 | Inoue | A61F 2/07 623/1.15 |
| 6,325,798 | B1 | 12/2001 | Edwards et al. | |
| 6,398,758 | B1 | 6/2002 | Jacobsen et al. | |
| 6,514,282 | B1 * | 2/2003 | Inoue | A61F 2/95 623/1.13 |
| 6,537,288 | B2 * | 3/2003 | Vargas | A61B 17/11 606/153 |
| 6,740,333 | B2 * | 5/2004 | Beckett | A61K 9/02 424/436 |
| 6,926,724 | B1 * | 8/2005 | Chu | A61B 17/11 606/153 |
| 6,962,595 | B1 * | 11/2005 | Chamness | A61B 17/12013 606/153 |
| 7,122,058 | B2 | 10/2006 | Levine et al. | |
| 7,211,114 | B2 | 5/2007 | Bessler et al. | |
| 7,267,694 | B2 | 9/2007 | Levine et al. | |
| 7,306,614 | B2 * | 12/2007 | Weller | A61B 17/0482 606/151 |
| 7,790,946 | B2 | 9/2010 | Mulligan | |
| 8,109,895 | B2 * | 2/2012 | Williams | A61F 5/0036 604/8 |
| 8,388,586 | B2 | 3/2013 | Weig | |
| 8,491,612 | B2 * | 7/2013 | Stopek | A61B 17/11 606/153 |
| 8,636,810 | B2 * | 1/2014 | Rousseau | A61B 17/11 623/23.68 |
| 8,690,817 | B2 * | 4/2014 | Assaf | A61M 27/002 604/8 |
| 8,790,322 | B2 * | 7/2014 | Matar | A61F 5/449 604/332 |
| 8,926,576 | B2 | 1/2015 | Mikkaichi | |
| 9,827,135 | B2 * | 11/2017 | Fong | A61F 5/4408 |
| 2004/0034364 | A1 | 2/2004 | Snyder | |
| 2004/0039348 | A1 | 2/2004 | Kim et al. | |
| 2004/0093026 | A1 * | 5/2004 | Weidenhagen | A61M 1/0023 606/215 |
| 2005/0228409 | A1 * | 10/2005 | Coppi | A61F 2/064 606/153 |
| 2007/0282161 | A1 | 12/2007 | Ferguson et al. | |
| 2008/0208325 | A1 * | 8/2008 | Helmus | A61L 27/427 623/1.44 |
| 2008/0215076 | A1 * | 9/2008 | Baker | A61B 17/1114 606/154 |
| 2008/0262449 | A1 | 10/2008 | Shah et al. | |
| 2009/0018606 | A1 | 1/2009 | Sparks et al. | |
| 2010/0010518 | A1 * | 1/2010 | Stopek | A61B 17/11 606/153 |
| 2010/0010519 | A1 * | 1/2010 | Stopek | A61B 17/11 606/154 |
| 2010/0022976 | A1 | 1/2010 | Weig | |
| 2011/0295288 | A1 | 12/2011 | Khosrovaninejad | |
| 2013/0023840 | A1 | 1/2013 | Loske et al. | |
| 2013/0066286 | A1 | 3/2013 | Croizat et al. | |
| 2013/0079890 | A1 * | 3/2013 | Rousseau | A61F 2/04 623/23.68 |
| 2013/0158463 | A1 * | 6/2013 | Assaf | A61B 17/1114 604/8 |
| 2013/0190706 | A1 * | 7/2013 | Kleiner | A61F 13/00021 604/319 |
| 2013/0204216 | A1 * | 8/2013 | Matar | A61F 5/448 604/342 |
| 2013/0274717 | A1 | 10/2013 | Dunn | |
| 2013/0274770 | A1 * | 10/2013 | Baker | A61B 17/068 606/151 |
| 2013/0304101 | A1 * | 11/2013 | Stopek | A61B 17/11 606/153 |
| 2014/0222039 | A1 | 8/2014 | Khosrovaninejad | |
| 2015/0038987 | A1 | 2/2015 | Harris et al. | |
| 2015/0148785 | A1 * | 5/2015 | Kleiner | A61M 1/0088 604/543 |
| 2015/0250979 | A1 | 9/2015 | Loske | |
| 2016/0030227 | A1 * | 2/2016 | Bronnimann | A61F 5/449 604/338 |
| 2016/0045358 | A1 * | 2/2016 | Bronnimann | A61F 5/445 604/339 |
| 2016/0045359 | A1 * | 2/2016 | Bronnimann | A61F 5/445 604/338 |
| 2017/0071780 | A1 * | 3/2017 | Fong | A61F 5/449 |

FOREIGN PATENT DOCUMENTS

| | | |
|---|---|---|
| JP | 2014500083 A | 1/2014 |
| JP | 2014527854 A | 10/2014 |

OTHER PUBLICATIONS

Office Action issued in related Chinese Patent Application No. 201680061127.1 dated Mar. 27, 2020.

Andreas Thalheimer, MD. et al. "Morbidity of Temporary Loop Ileostomy in Patients With Colorectal Cancer", Diseases of the Colon & Rectum, Jul. 2006, vol. 49, No. 7, pp. 1011-1017.

Annelien N. Morks, et al. "Can intraluminal devices prevent or reduce colorectal anastomotic leakage: A review", World J Gastroenterol, Oct. 28, 2011, 17(40), pp. 4461-4469.

Benjamin D. Shogan et al. "Do We Really Know Why Colorectal Anastomoses Leak?" J Gastrointest Surg (2013) 17:1698-1707.

International Search Report and Written Opinion dated Dec. 7, 2016 in corresponding International Application No. PCT/US16/51985.

Orit Kaidar-Person, MD et al. "Complications of Construction and Closure of Temporary Loop Ileostomy", J Am Coll Surg, vol. 201, No. 5, Nov. 2005, pp. 759-773.

Vijayraj Patil et al. "Comparison between Tube Ileostomy and Loop Ileostomy as a Diversion Procedure", ISRN Surgery, vol. 2012, Article ID 547523, 5 pages.

Office Action issued in related Japanese Patent Application No. 2018-532546 dated Jul. 13, 2020.

Office Action issued in related Australian Patent Application No. 2016323425 dated May 27, 2020.

* cited by examiner

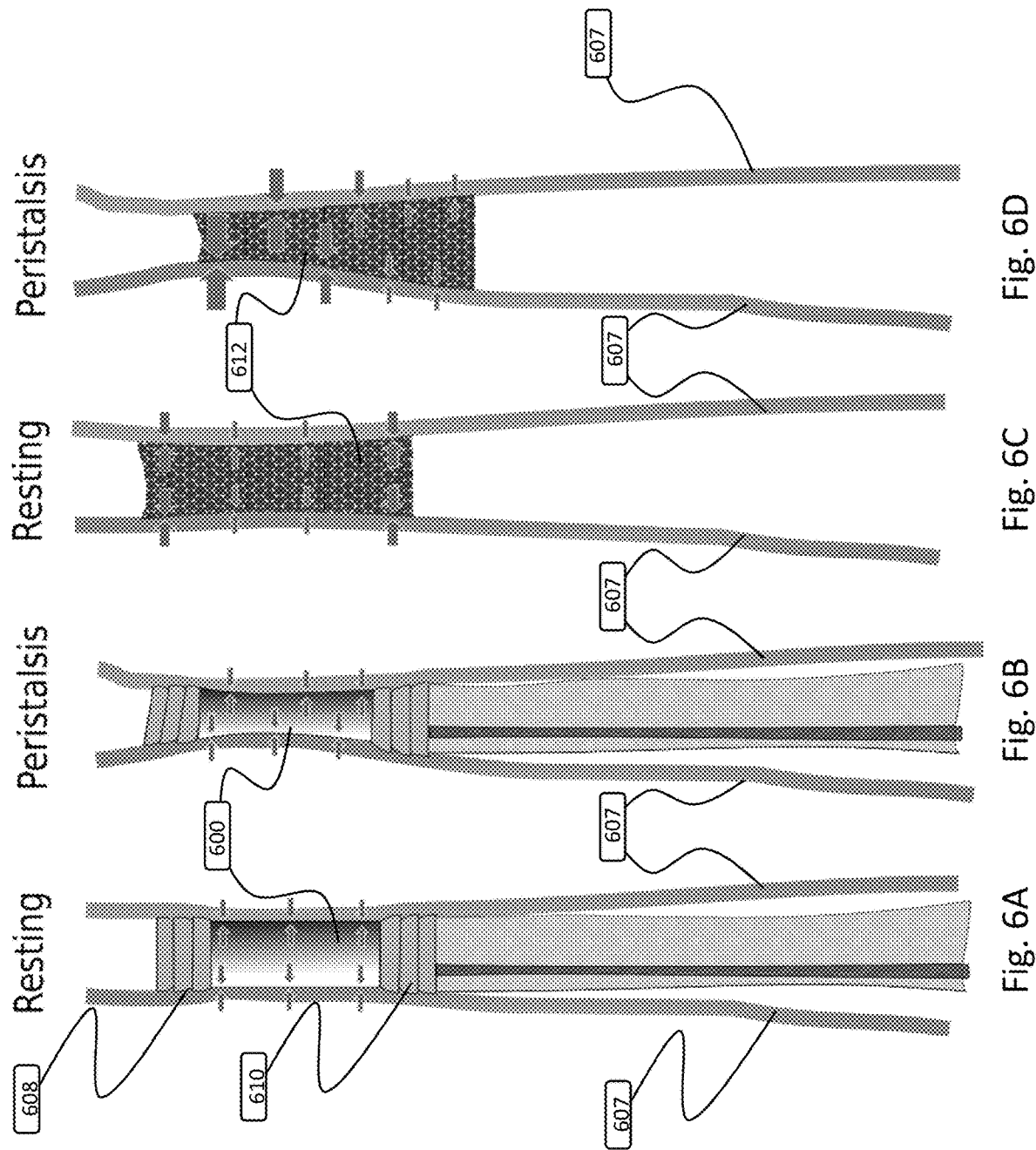

DEVICES AND METHODS FOR ANCHORING A SHEATH IN A TISSUE CAVITY

This application is a continuation of U.S. application Ser. No. 15/266,976, filed Sep. 15, 2016, which claims priority to U.S. Provisional Application No. 62/283,877 filed Sep. 15, 2015, the contents of which are hereby incorporated by reference in their entirety.

BACKGROUND

1. Technical Field

The field of the currently claimed embodiments of this invention relates to medical devices, and more particularly to anchoring medical devices within a tissue cavity.

2. Discussion of Related Art

The need for temporary protection of the bowel lumen from fecal flow after surgical bowel resection and anastomosis or when the bowel wall is damaged has traditionally been accomplished by the creation of an external diversion of the bowel through the creation of an ostomy. An ostomy is a purposeful anastomosis between a segment of the gastrointestinal (GI) tract and the skin of the anterior abdominal wall. An ostomy can be created virtually anywhere along the GI tract. For diversion of the fecal stream, the most common ostomies involve the distal small intestine (e.g., ileostomy) and large intestine (e.g., colostomy). Ostomies are performed in 300,000 patients in the US and over 2 million patients globally, but this surgery is complicated by high morbidity, mortality, and severe impact on a patient's quality of life. Although many ostomies are intended to be temporary, as many as ⅓ of temporary ostomies are never reversed. Accordingly, there is a need for improved method and devices to provide a less morbid alternative for fecal diversion.

One of the major indications for a temporary ostomy is to protect a bowel anastomosis from enteric contents that can lead to anastomotic leaks. An anastamotic leak is defined as a defect of the intestinal wall at the anastomotic site leading to a communication between the intra- and extraluminal compartments. Anastamotic leaks after bowel surgery is a major complication. The overall incidence of colorectal anastomotic leak varies widely in the literature, ranging from 1 to 24%. Leaks can cause severe complications such as loss of the anastomosis, sepsis, and death. Even in those cases where the anastomosis is salvaged, poor compliance in the neorectum can lead to a poor functional outcome. In many large studies, anastamotic leaks has been shown to be associated with a pelvic sepsis at a rate of 50%. By protecting the anastomosis from fecal flow, anastamotic leaks may be prevented or their morbidity mitigated. In addition, even after an anastamotic leak has occurred, protection from fecal flow can make the anastamotic leak less severe and aid in healing of the leak. There are several risk factors for the development of an anastamotic leak. The most significant risk factor is the level of the anastomosis, with the leak rate increasing as the distance from the anastomosis to the anus decreases. Other than meticulous technique in creating the anastomosis, the major strategy to prevent and treat anastamotic leaks during complicated or high-risk cases involving bowel resection is to divert fecal flow. This is accomplished by having the flow of gastric contents diverted using an ostomy created in the bowel proximal to the anastomosis. Proximal in the bowel is defined as higher up in the GI tract towards the mouth, distal in the bowel is defined as lower down in the GI tract towards the anus. This ostomy can be either an end ostomy such as an end colostomy or end ileostomy or can be a diverting loop ileostomy that does not completely disrupt bowel continuity.

A temporary diverting ostomy and its closure has its own set of complications and morbidities including dehydration due to high output, difficulty with ostomy care, stricture at the closure site, wound infections, and incisional hernias. Complication rates of ostomies range between 5% and 100%. The complications can be divided into minor complications, which do not require surgical intervention, and major complications requiring surgical intervention. Major complications include stenosis, small bowel obstruction, retraction, necrosis, prolapse, stricture, fistula, and parastomal hernia. In some cases, such as partial small bowel obstruction, the patient can first be treated conservatively and surgical intervention may be avoided. Major complications such as ostomy necrosis that extends more than a few millimeters, surgical intervention is mandatory. Minor complications include dermatitis, electrolyte imbalance, and dehydration from high ostomy output, although the last often necessitates early closure of the ostomy. For major complications, additional costs and morbidity associated with additional operations or hospitalizations can be significant. Even for minor complications, treating complications and providing ostomy education can be burdensome to healthcare providers and patients. Some complications such as hernia, prolapse, and stenosis may become chronic and often require multiple corrective operations and associated costs. Ostomies also significantly reduce a patient's quality of life. Fecal output from the ostomy is collected into an ostomy bag attached to the patient's abdomen. These bags need to be emptied and replaced regularly to properly care for the ostomy and prevent unintentional discharge of fecal material.

Furthermore, the reversal of an ostomy is a surgical procedure fraught with potential complications, as often times the abdominal compartment has dense adhesions that make re-establishment of normal bowel continuity both costly and potentially morbid. In addition to expenses associated with taking patients to the operating room, patients typically require a hospitalization of 2-4 days post-procedure to allow for support until bowel function returns. Furthermore, the reversal of an ostomy may be difficult or impossible in some patients, requiring the patient to live the rest of their life with an ostomy. The repaired bowel after ostomy takedown may also develop a leak at the repair site or anastomotic site in cases of loop ileostomies or in cases of end ostomy reattachment, respectively.

Besides anastomotic protection, there are other potential indications for temporary fecal diversion. These include: 1) treatment of an anastomotic leak after it has occurred, 2) diverticulitis, 3) inflammatory bowel diseases such as Crohn's or Ulcerative Colitis, 4) intestinal perforation and 5) other less common instances of bowel injury where fecal diversion could be useful such as in cases of ischemic bowel disease, bowel contusion injury from trauma, or non-healing perineal/perianal wounds. When a leak or bowel perforation has occurred such as in cases of anastomotic leak and diverticulitis as examples, treatment with fecal diversion can reduce the severity and extent of the condition. Thus, these patient may heal their leak/perforation faster and not develop more severe complications when continued fecal flow contamination of the affected site is mitigated. Inflammatory conditions of the bowel wall such as Crohn's disease or Ulcerative Colitis can make the intestinal lining susceptible to damage from fecal flow. Continued fecal flow can further inflame and contaminate the bowel wall and lead to worsening of patient's overall disease or even frank perforation of the bowel wall. Protection from fecal flow allows the inflamed sections of bowel to rest and heal, and potentially fecal diversion could reduce recovery time, hospitalization time, and limit severe complications such as perforations or fistula formation. Patients with these conditions may not be good candidates for surgery due to their concomitant conditions or sepsis; thus, performing major surgery to create an ostomy can be morbid in these cases. Accordingly, there is a need for improved method and devices to provide a less morbid alternative for fecal diversion.

In the past, the concept of an intraluminal sheath for internal fecal diversion has been described (U.S. Pat. Nos. 4,716,900; 4,905,693; U.S. Patent Application Publication No. 2010/0010519). The principal challenge has been developing a device that can anchor securely within the bowel without harming the bowel wall itself and effectively accomplishing air and fluid tight fecal flow diversion. Staple and suture based techniques for devices such as those described by Ravo et al. (U.S. Pat. No. 4,716,900), Ravo (U.S. Pat. No. 4,905,693), and Stopek et al. (U.S. Patent Application Publication No. 2010/0010519) are both potentially harmful to the area of bowel damage from traction and cannot achieve effective sheath anchoring without major surgery. Other methods of anchoring within the bowel have also been described that dependent on scar formation to secure an anchor in place such as the device described by Baker (U.S. Patent Application Publication No. 2008/0215076). This method however is not easily reversible and depends on the body's scar forming ability which may be compromised in some patients for secure anchoring. There have also been stent-based anchors such as the devices described by Khosrovaninejad (U.S. Patent Application Publication No. 2011/0295288), Levine et al. (U.S. Pat. No. 7,267,694), Rockey (U.S. Pat. No. 4,641,653) and Bessler et al. (U.S. Pat. No. 7,211,114), but stents do not provide enough anchor strength to hold the sheath firmly in place during bowel peristalsis as evidenced by their high rate of premature expulsion, and may further damage the bowel wall due to the necessary rigidity and expansion force they exert to provide anchoring. Others have attempted using a fixed biodegradable ring anchor placed outside and around the bowel wall such as Assaf et al. (U.S. Patent Application Publication No. 2013/0158463), but this approaches also requires major surgery for placement and exposes the bowel to potential erosion and damage due to pressure points exerted on the bowel wall. In addition, the necessity of creating a substantial air and fluid tight bypass of fecal contents has also been a technical challenge. Inflatable balloon types of seals such as those described by Assaf et al. (U.S. Patent Application Publication No. 2013/0158463) and Weig (U.S. Pat. No. 8,388,586 and U.S. Patent Application Publication No. 2010/0022976) have been described to try and achieve air and fluid tight seals within the intestines, but these again require potentially harmful expansible forces and pressure on the bowel wall to form a seal and often fail to achieve an adequate air and fluid tight barrier to enteric flow.

Negative pressure wound therapy has been used to treat anastomotic leaks in the past, and these dressings typically utilize a foam interface over the damaged area of bowel covered by an occlusive barrier connected to a negative pressure source. Devices specifically designed to treat wounds and provide negative pressure treatment in the intestine or body cavities have been described (U.S. Patent Application Publication No. 2013/0190706, U.S. Pat. No. 8,926,576, and U.S. Patent Application Publication No. 2015/0250979). Importantly, these devices are designed to be placed and to deliver negative pressure at the site of an anastomosis or tissue damage and as a result can cause further damage to the area of the anastomosis or tissue damage when longitudinal forces are placed on these devices or negative pressure ischemia is induced. These devices are not designed to protect the bowel lumen distal to the site of placement. These types of dressing devices for negative pressure wound therapy have difficulty establishing and maintaining air tight seals and become frequently dislodged due to their lack of adequate sealing mechanisms. Furthermore, these devices are not configured in a way to withstand the additional longitudinal forces that can displace the device with the addition of a protective sheath. Lastly, these devices employ expandable wire-stent based designs to provide semi-rigid structure (U.S. Patent Application Publication No. 2013/0190706, U.S. Pat. No. 8,926,576, and U.S. Patent Application Publication No. 2015/0250979) that can create tissue damage and make them more prone to expulsion from the bowel due to peristaltic forces. Khosrovaninejad (U.S. Patent Application Publication No. 2014/0222039) has used negative pressure suction to attempt to anchor a protective sleeve within the bowel. The major issues with this device are that the attachment and anchoring of the device is dependent on the adherence forces of negative pressure delivered via perforations and the radial expansion force of a stent-based design. Perforations do not allow for adequate friction force to be generated to substantially fix a device in place and resist the expulsion forces of the bowl. Thus, this device is designed to be expulsed from the body after several days and must be placed very high above an area to be treated. Furthermore, the expansile stent-based design suffers from the same issues of other stent-based designs of potential bowel damage and expulsion. Accordingly, there needs to be a device and method that can securely anchor within a body cavity in a controlled fashion that has an improved safety profile and increased anchoring strength and reliability.

SUMMARY

According to some embodiments of the invention, an anchoring system includes a sleeve having an inner surface defining a first lumen, a first annular sealing mechanism disposed at a proximal end of the sleeve, and a second annular sealing mechanism disposed at a distal end of the sleeve. The anchoring system further includes a pressure tube in fluid connection with an outer surface of the sleeve, a sheath in mechanical connection with the sleeve, the sheath forming a second lumen, the second lumen being in fluid connection with the first lumen, and open-cell foam disposed on the outer surface of the sleeve. Application of negative pressure to the pressure tube causes a seal to form between the first and second annular sealing mechanisms and an inner surface of a tissue cavity. Application of negative pressure to the pressure tube also creates a frictional force that resists displacement of the sleeve.

According to some embodiments of the invention, the application of negative pressure to the pressure tube brings the open-cell foam disposed on the outer surface of the sleeve into contact with the inner surface of the tissue cavity thereby creating the frictional force that resists displacement of the sleeve.

According to some embodiments of the invention, the first and second annular sealing mechanisms form a substantially airtight and fluid-tight seal with the inner surface of the tissue cavity. According to some embodiments, the first and second sealing mechanisms comprise a rounded protrusion or multiple protrusions placed in series at each end of the sleeve that are compressible. According to some embodiments, each of the first and second sealing mechanisms comprises a plurality of concentric fins that form a series of concentric seals. According to some embodiments, each of the first and second sealing mechanisms comprises a plurality of concentric protrusions that form a series of concentric seals.

According to some embodiments of the invention, the sheath protects the inner surface of the tissue cavity from fecal flow distal to the sleeve. According to some embodiments, the first lumen has a diameter between approximately 1 cm and approximately 6 cm. According to some embodiments, the outer surface of the sleeve has a diameter between approximately 1.1 cm and approximately 6.1 cm. According to some embodiments, the sleeve comprises a flexible material having a Shore A hardness between about 20 A and about 70 A. According to some embodiments, the sleeve has a length that is between about 3 cm and about 25 cm. According to some embodiments, the sleeve has a tubular wall thickness of between about 0.1 mm and about 8 mm. According to some embodiments, the sleeve has a tubular wall thickness that is between about 0.2 mm and about 5 mm.

According to some embodiments of the invention, the open-cell foam comprises a material having an average pore size between about 50 microns and about 1000 microns. According to some embodiments, the open-cell foam comprises a material having an average pore size between about 300 microns and about 600 microns. According to some embodiments, the open-cell foam comprises a material having an average pore size between about 100 microns and about 300 microns. According to some embodiments, the open-cell foam is compressible by peristaltic contractions of a patient's bowel. According to some embodiments, the open-cell foam comprises polyvinyl alcohol, polyurethane foam, or other synthetic polymer. According to some embodiments, the open-cell foam has a tensile strength of at least 50 kpa. According to some embodiments, the open-cell foam has a thickness of between 2 mm and 150 mm. According to some embodiments, the open-cell foam comprises a single tubular piece of foam.

According to some embodiments of the invention, the first and second annular sealing mechanisms comprise a flexible material having a Shore A hardness between about 20 A and about 70 A. According to some embodiments, the first and second annular sealing mechanisms have an annular diameter that is greater than an annular diameter of the open-cell foam dispersed around the sleeve. According to some embodiments, the first and second annular sealing mechanisms comprise one or more tapered fins placed in series on each end of the sleeve with an orientation directed away from a center of the sleeve so that the one or more tapered fins lie flat against the inner surface of the tissue cavity when negative pressure is delivered through the pressure tube. According to some embodiments, the first and second annular sealing mechanisms comprise a rounded protrusion or multiple protrusions placed in series at each end of the sleeve that are compressible.

According to some embodiments of the invention, the anchoring system further includes a negative pressure source, wherein negative pressure is applied to the pressure tube by the negative pressure source to maintain constant negative pressure at a level between −50 mmHg and −200 mmHg. According to some embodiments of the invention, the anchoring system further includes an irrigation tube in fluid connection with the outer surface of the sleeve. According to some embodiments of the invention, the anchoring system further includes an irrigation system in fluid connection with the pressure tube, wherein the irrigation system introduces a fluid into the pressure tube for irrigation.

According to some embodiments of the invention, the sheath has a length that allows it to extend outside the tissue cavity. According to some embodiments, wherein the first lumen, second lumen, and first and second annular sealing mechanisms are compressible by normal peristaltic forces of a patient's bowel. According to some embodiments, a diameter of the first annular sealing mechanism and the second annular sealing mechanism is less than or equal to a diameter of the tissue cavity in which the sheath is to be anchored. According to some embodiments, the anchoring system is configured so that traction on the sheath can be used to remove the anchoring system from the body cavity. According to some embodiments, the sheath has a wall thickness that is between about 50 microns and about 5 mm. According to some embodiments, the sheath has a length that is between about 8 inches and about 72 inches. According to some embodiments, the sheath has markings along its length that indicate the length of sheath within the tissue cavity after placement. According to some embodiments, the sheath is comprised of silicone, polyurethane, thermoplastic elastomer, rubber, or other polymer.

According to some embodiments of the invention, the pressure tube is attached to the sheath along its length. According to some embodiments, the pressure tube is disposed within a wall of the sheath. According to some embodiments, the pressure tube is integrated into the sheath and comprises a same material as the sheath. According to some embodiments, the pressure tube is disposed within an additional lumen along the length of the sheath.

According to some embodiments of the invention, the sleeve, first and second sealing mechanisms, and sheath are comprised of one or more of silicone, polyurethane, thermoplastic elastomer, rubber, rubber-like material, or other polymer.

According to some embodiments of the invention, the anchoring system further includes a plurality of pressure tubes in fluid connection with the outer surface of the sleeve.

According to some embodiments of the invention, the anchoring system further includes an effluence bag in fluid connection with the sheath, the effluence bag configured to receive the content of the sheath. According to some embodiments, the effluence bag is detachable.

According to some embodiments of the invention, the sleeve, the first annular sealing mechanism, and second annular form a first anchoring element, and the anchoring system further includes a second anchoring element in mechanical connection with the sheath, the second anchoring element disposed apart from and distal to the first anchoring element, and a port disposed between the first anchoring element and the second anchoring element. The sheath, the first anchoring element, and the second anchoring element create a sealed off space between the first and second anchoring elements, the sheath, and the inner surface of the tissue cavity, and the port is in communication with the sealed off space to allow access from outside a patient's body for fluid delivery and withdrawal. According to some embodiments, the sheath is divided into multiple anchoring segments having an independent negative pressure supply.

According to some embodiments, the fluid administered is an anti-inflammatory, chemotherapeutic, antimicrobial, radiologic contrast, or cleansing solution. According to some embodiments, the sleeve is divided by additional sealing mechanisms to create multiple anchoring segments. According to some embodiments, multiple pieces of foam are dispersed around each anchoring segment. According to some embodiments, each of the anchoring segments has an independent negative pressure supply.

According to some embodiments of the invention, the sleeve and first and second annular sealing elements are made from a single injection mold using a single material. According to some embodiments, the sheath comprises a releasable, fluid-tight sheath connector at between 8 inches and 36 inches from the second annular sealing mechanism. According to some embodiments, the sheath comprises a separation junction at between 8 inches and 36 inches from the second annular sealing mechanism. According to some embodiments, the anchoring system is configured to be positioned in the tissue cavity using an endoscope. According to some embodiments, the anchoring system is configured to be attached to a releasable clip on an end of the endoscope that can release the anchoring system from the endoscope from outside a patient's body. According to some embodiments, the tissue cavity is bowel comprising an anastomosis, and wherein the anchoring system is positioned within the bowel such that the anastomosis is located distal in the bowel to the second annular sealing mechanism. According to some embodiments, the anchoring system further includes an irrigation system in fluid connection with the pressure tube, wherein the irrigation system introduces a fluid into the pressure tube for irrigation.

According to some embodiments of the invention, a delivery system includes a flexible tubular membrane that encases the anchoring system according to embodiments of the invention, and a semi-rigid tube pusher with a proximal end, a distal end, and a center. The anchoring system is configured to be pushed into position by advancing the semi-rigid tube pusher into a patient's bowel, and the flexible tubular membrane invaginates down the proximal end and out the distal end of the semi-rigid tube pusher.

According to some embodiments of the invention, the delivery system compresses the anchoring system and holds the anchoring system to the semi-rigid tube pusher when longitudinal traction is applied to the flexible tubular membrane. According to some embodiments, the delivery system further includes a flexible member that can be detached from a semi-rigid tube pusher and extracted from a patient's body through the center of the semi-rigid tube pusher after placement of the anchoring system.

According to some embodiments of the invention, a temporary anchoring device for diverting fecal flow through a bowel lumen includes a sleeve having an inner surface defining a first lumen, a first annular sealing mechanism disposed at a proximal end of the sleeve, and a second annular sealing mechanism disposed at a distal end of the sleeve. The temporary anchoring device further includes a pressure tube in fluid connection with an outer surface of the sleeve, a sheath in mechanical connection with the sleeve, the sheath forming a second lumen, the second lumen being in fluid connection with the first lumen, and air conducting rough surface material disposed on the outer surface of the sleeve. Application of negative pressure to the pressure tube causes a seal to form between the first and second annular sealing mechanisms and an inner surface of the bowel lumen, and the application of negative pressure to the pressure tube creates a frictional force that resists displacement of the sleeve.

According to some embodiments, the air conducting rough material is a stacked mesh matrix, a honey-comb lattice of interconnected channels oriented in a radial fashion around the sleeve, gauze, fabric, or a three-dimensional woven material.

According to some embodiments of the invention, a method for anchoring a sheath in a tissue cavity, the sheath being in mechanical connection with a sleeve, the sleeve having an outer surface comprising foam for contacting an inner wall of the tissue cavity, and a sealing mechanism for isolating a portion of the tissue cavity adjacent to the sleeve from a remainder of the tissue cavity, includes inserting the sleeve in the tissue cavity. The method further includes applying a negative pressure to a region between an outer surface of the sleeve and an inner surface of the isolated portion of the tissue cavity to create a frictional force between the outer surface of the sleeve and the inner surface of the tissue cavity.

BRIEF DESCRIPTION OF THE DRAWINGS

Further objectives and advantages will become apparent from a consideration of the description, drawings, and examples.

FIG. 6A shows an anchoring system according to some embodiments of the invention anchored within the bowel when the bowel is at rest with arrows showing the relative normal forces exerted by the anchoring system and the bowel wall.

FIG. 6B shows the anchoring system during peristalsis with arrows showing the relative normal forces exerted by the anchoring system and the bowel wall.

FIG. 6C shows a semi-rigid, stent-like device in a bowel at rest with arrows showing the relative normal forces exerted by the device and the bowel wall.

FIG. 6D shows the stent during peristalsis with arrows showing the relative normal forces exerted by the device and the bowel wall.

DETAILED DESCRIPTION

Figure 1:
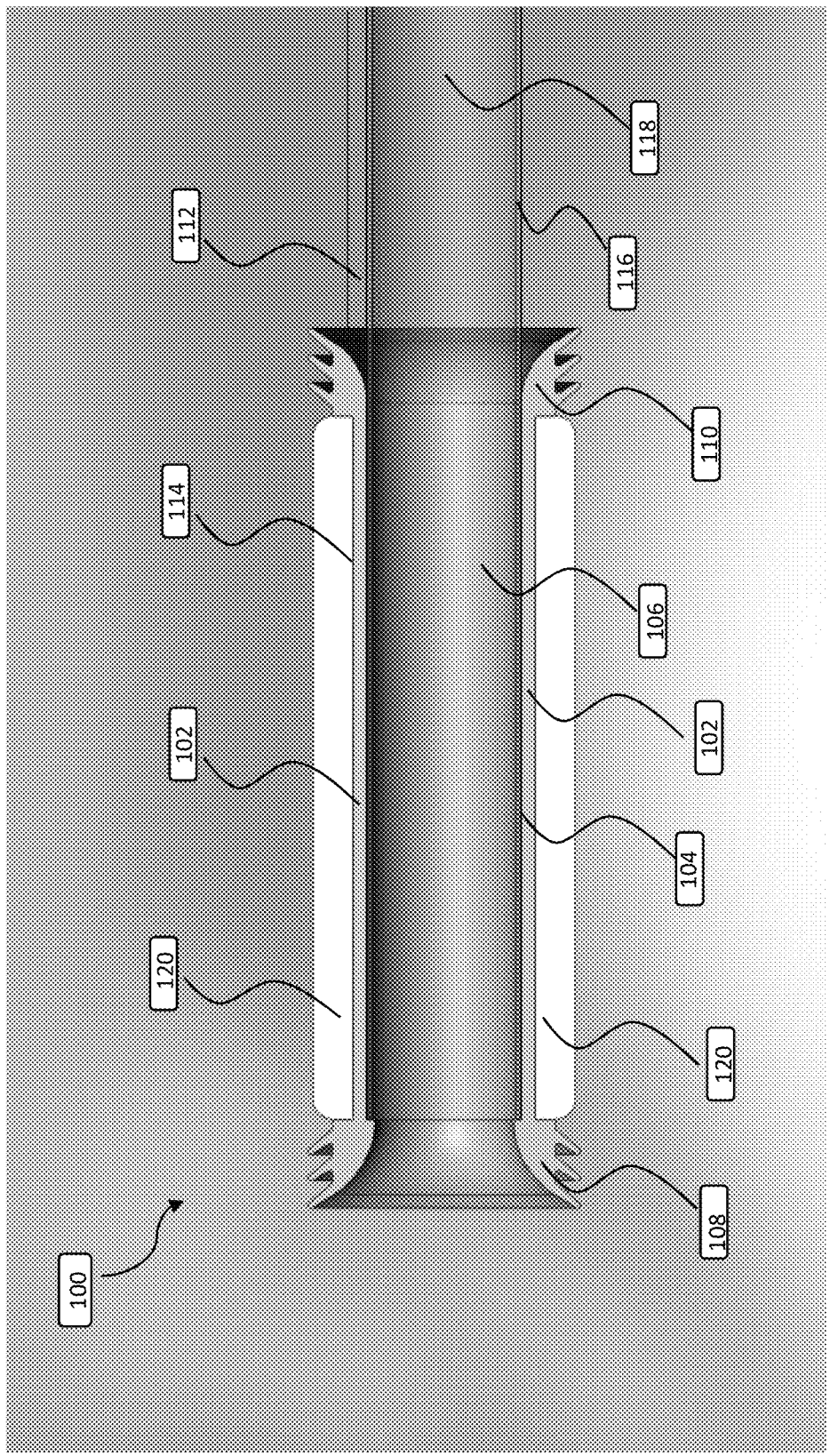
FIG. 1 is a schematic illustration of an anchoring system according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Disclosed herein are systems and methods for anchoring a protective sheath within the bowel proximal to a region of bowel that requires protection from fecal flow, such as a bowel anastomosis or area of bowel damage. The system and methods can make temporary fecal diversion ostomy surgery unnecessary in most patients, as it provides internal fecal diversion and accomplishes the same overall objective as a temporary ostomy by protecting the distal segment of bowel from fecal flow. In addition, we disclose additional configurations of this system that enable drug delivery to the intestinal lumen.

The system includes an anchoring mechanism that allows for non-traumatic and reversible anchoring of a sheath within the GI tract that diverts fecal contents away from the anastomotic site or area of damaged bowel. The device is designed to be left in place for a period of a few days to four weeks, and then removed completely from the patient after healing has occurred or diversion is no longer required. While the device and method are described here in the context of securely anchoring a sleeve within the GI tract for the purpose of therapeutic benefit such as diverting bowel contents, the device and method for anchoring may also have applications in other regions of the body where secure anchoring within a tissue cavity is desired. It is important to emphasize that this is a device designed to be substantially and securely anchored in place within the bowel and to prevent substantial device migration until the device is actively disengaged and removed by the clinician. This is in contrast to other non-surgically attached sheath based protection devices that are unable to be securely anchored and are slowly extruded from the bowel over time because they cannot maintain the same high level of anchoring strength required to resist bowel expulsion forces. The unique design of the device disclosed herein allows for it to anchor in place within the bowel without dislodgement, without damaging the bowel wall, without the need for a surgical fixation such as suturing or stapling, and without the need for a permanent implant. Each of these features are described in more detail below.

According to some embodiments, the device includes a negative pressure based anchoring system that prevents a sleeve from becoming dislodged from the inner surface of the bowel. The sleeve is connected to a sheath and acts, in combination with the sheath, as a protective barrier between the GI tract and the GI contents flowing through the sleeve and sheath. According to some embodiments, the device includes a pneumatic system for applying negative pressure to the anchor system. The device in some embodiments includes an external effluence bag to collect GI content that flows through the sleeve and sheath. However, an external effluence bag is not required for the device to function. In some embodiments, the device has a sheath that is open just external to the anal sphincter and feces can be passed through this opening. In this embodiment, the anal sphincter constricts around the sheath and provides some continence and a collection bag is not required.

According to some embodiments, the anchoring portion of the device is positioned in the GI tract on the proximal side of an anastomosis or proximal to the area of damaged bowel. The proximal side is the side that is "upstream" in terms of the flow of GI content through the GI tract. This is in contrast to anastomosis or wound treatment systems that are configured to be applied directly to an anastomosis or wound site. This device is configured to be anchored in healthy undamaged bowel. Constant negative pressure is maintained via a pneumatic interface connected to the anchoring system and dispersed through an open cell reticulated foam interface. Special sealing elements at the end of the sleeve create a negative pressure space between the outer surface of the sleeve containing the foam interface and the bowel wall. When negative pressure is applied, the pressure gradient acts through the foam to create adhesive and friction forces between the GI tract and the anchoring system. These adhesive and friction forces created by the negative pressure-sponge interface enable the anchoring system to maintain a relatively fixed position in the bowel that is much greater than other non-surgically fixated sheath anchoring systems previously described. When a user is ready to remove the device, normal atmospheric pressure between the anchoring device and bowel can be reestablished, allowing the device to move through the GI tract with minimal friction. The device and method of fixation do not require suturing, stapling, biodegradable implants, or other invasive anchoring techniques, and create minimal trauma to the bowel. Thus, disclosed herein are a method and device for securely fixing a sleeve within the bowel lumen in a manner that does not substantially damage the bowel wall, and that allows fixation to be easily reversed for device removal.

In accordance with the features of the embodiments of the invention, the device for anchoring the sleeve within the bowel can be described as having a hollow body with multiple seals on each end and porous material on the external surface of the hollow body such that upon application of negative pressure to the external surface of the hollow body, an adhesive force forms between the bowel wall and hollow body. A tube can deliver negative pressure to the sealing member. A protective sleeve can be attached to the sealing member and a collection system can collect contents which pass through the sealing member.

FIG. 1 shows a cross-sectional view of the anchor portion of the anchoring system according to some embodiments of the invention. The anchoring system 100 includes a sleeve 102 having an inner surface 104 defining a lumen 106. A first annular sealing mechanism 108 is disposed at a proximal end of the sleeve 102, and a second annular sealing mechanism 110 is disposed at a distal end of the sleeve 102. For the device, proximal is defined as the part of the device farthest from where fecal matter exits the sheath (at an effluence bag, for example), and distal is defined as the part of the device that is closer to where fecal matter exits the sheath during regular fecal flow. This orientation convention is used because this is the relationship of flow through the device (from proximal to distal) and matches the orientation of the device within the bowel. A pressure tube 112 is in fluid connection with an outer surface 114 of the sleeve 102. A sheath 116 is in mechanical connection with the distal end of the sleeve 102, and forms a second lumen 118 that is in fluid connection with the first lumen 106. Open-cell foam 120 is disposed on the outer surface 114 of the sleeve 102. The application of negative pressure to the pressure tube 112 causes a seal to form between the first and second annular sealing mechanisms 108, 110 and an inner surface of the tissue cavity, and creates a frictional force that resists displacement of the sleeve 102.

Figure 2:
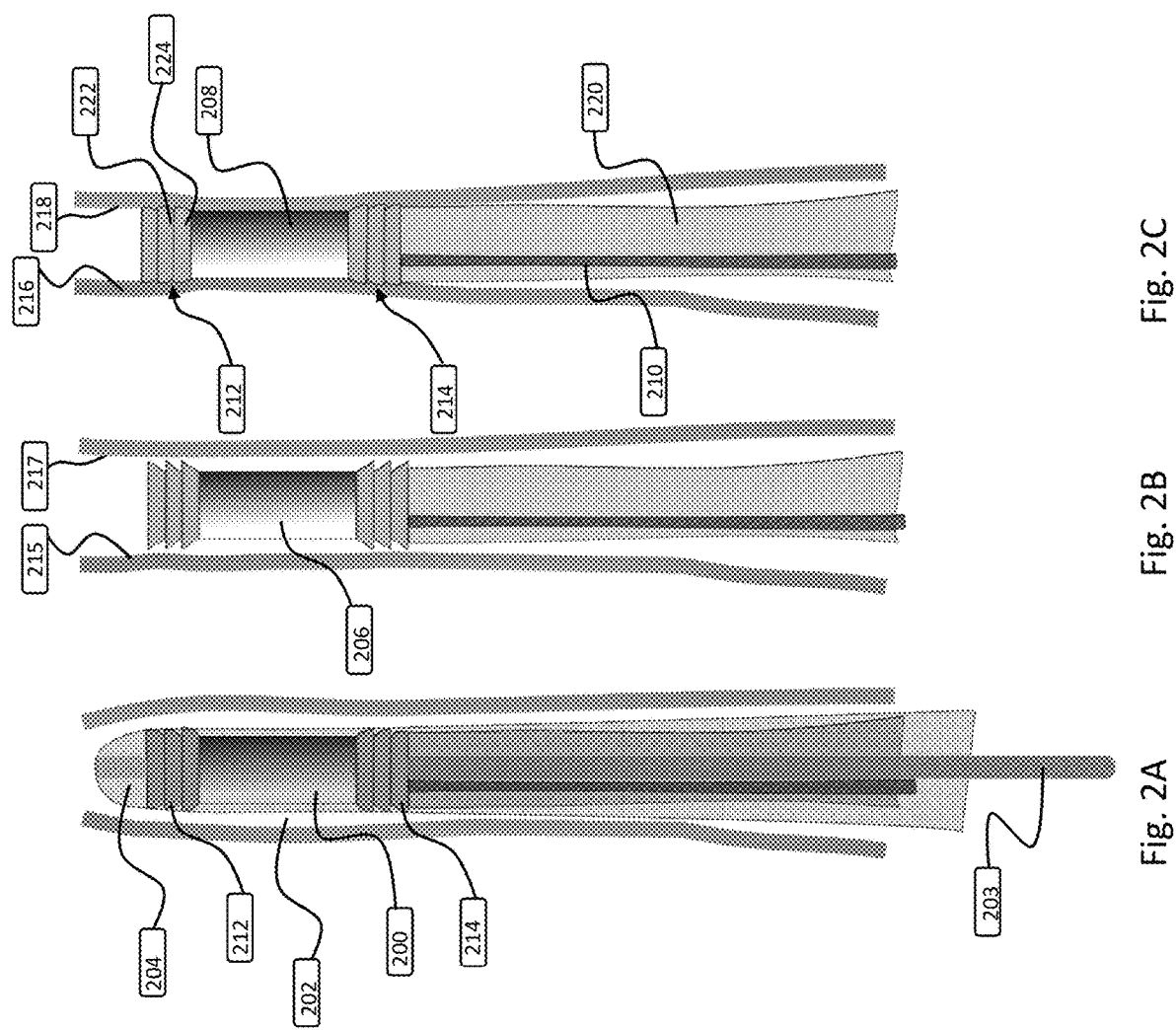
FIG. 2A illustrates a method for insertion of the anchoring system in a tissue cavity with a flexible member and semi-rigid tube pusher.
FIG. 2B illustrates the anchoring system detached from the delivery system (flexible member and pushing member removed) and in the desired position.
FIG. 2C illustrates the anchoring system once negative pressure is applied through the pressure tube with collapse of the bowel wall around the sealing members and anchor sleeve.

FIGS. 2A-2C illustrate a method for insertion and anchoring of the anchoring system. The anchor portion of the anchoring system 200 comprising the sleeve, sealing mechanisms 212, 214, and foam dispersed around the sleeve is transmitted through the tissue cavity 202 to the anchoring site. In the case of an anastomosis, the device is delivered to a position proximal to the anastomosis, such that the sleeve and sealing mechanisms are all proximal to the anastomosis. A semi-rigid tube pusher 203 is used to position the device in the appropriate position. A flexible membrane 204 covers the device and provides flattening of the sealing mechanisms 212, 214 to reduce friction during placement. The flexible membrane 204 also further reduces friction by covering the foam dispersed over the sleeve. The device may also be delivered using an endoscope or other delivery system. Example delivery systems are discussed in detail below.

Once the device is positioned at the desired location above the area requiring isolation from fecal flow by the sheath 220, it is detached from the delivery system, and the delivery system components including the semi-rigid tube pusher 203 and flexible membrane 204 are removed from the patient.

FIG. 2B illustrates the device 206 detached from the delivery system and in the desired position. FIG. 2C illustrates the device 208 once negative pressure is applied through the pressure tube 210. As air is removed from the space between the anchoring mechanisms on the outer surface of the sleeve, the inner walls of the tissue cavity are drawn toward the sleeve. As shown in FIG. 2B, unlike an anchor depending on expansion forces to provide fixation such as a stent, the device 206 can have some or all of its components' external diameter smaller than the inner diameter of the closed off tissue cavity inner wall 215, 217 in which it is to be anchored. The sealing mechanisms 212, 214 create a seal with the wall of the tissue cavity at either end of the sleeve. As shown in FIG. 2C, the sealing mechanisms 212, 214 comprise sealing elements 222, 224 that are structured to conform to the inner walls 216, 218 of the tissue cavity as negative pressure is applied, thereby creating a liquid-tight and air-tight seal. The flexibility of the sealing elements and the angle at which they protrude allows for them to fold down when negative pressure is applied to avoid creating pressure ischemia of the bowel wall, as illustrated in FIG. 2C. This allows the sealing elements to lie flat against the tissue surface, creating a seal with reduced pressure on the tissue at the interface between the sealing mechanisms 212, 214 and the tissue cavity wall 216, 218. The multiplicity of the sealing mechanisms' annular design (i.e., having multiple circular fins or protrusions) allows for redundancy in the seal created and the ability to accommodate irregularities in the contour of the inner tissue cavity wall 216, 218. In addition, the sealing elements have an external diameter that is greater than the external diameter of the foam. This allows for more reliable creation of a seal with the bowel when the bowel wall is sucked down during negative pressure activation.

The seals at both ends of the sleeve prevent air from entering the space between the sleeve and the cavity wall. The sealing mechanism 212 at the proximal end of the sleeve also diverts fluid and other GI content traveling through the tissue cavity into the central lumen of the sleeve in cases where the tissue cavity is the bowel. The GI content passes through the central lumen and into the sheath 220. The GI content is thus isolated from the anastomosis more distal in the GI tract. This prevents anastomotic contamination with fecal flow. The sealing elements in combination with negative pressure create an air and fluid tight bypass of GI contents that is superior to other methods such as inflatable cuffs that have been used in attempt to create an effective seal at the proximal end of an intraluminal bypass sheath.

Figure 3:
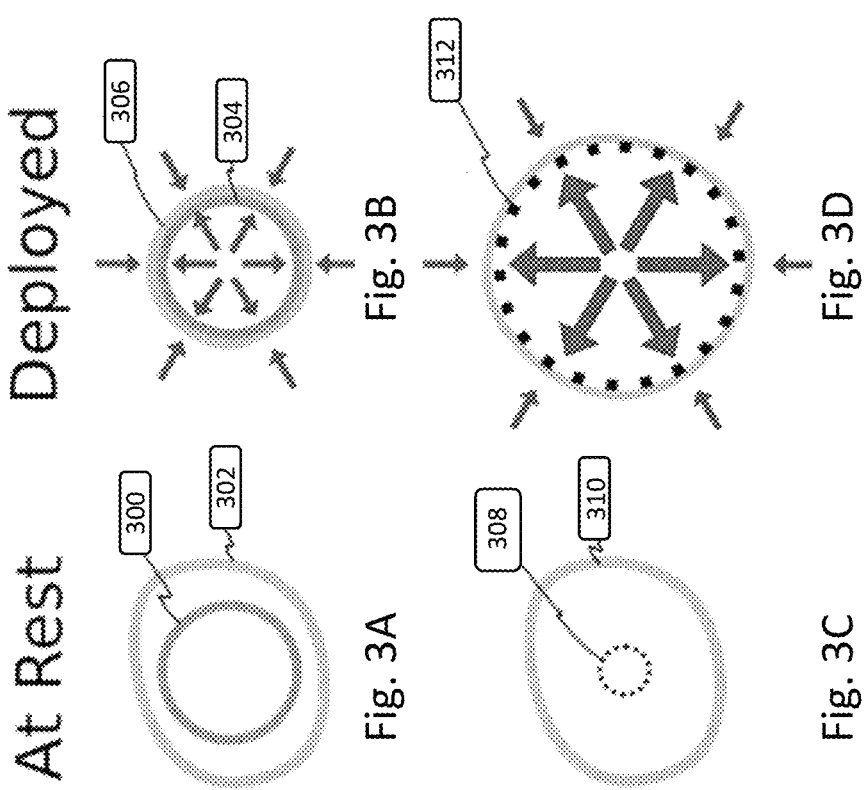
FIG. 3A shows the outer circumference of the foam surrounding the sleeve in a tissue cavity under normal pressure conditions.
FIG. 3B shows the foam and tissue when negative pressure is applied with arrows showing the relative normal force.
FIG. 3C shows an expandable stent in the bowel prior to deployment of the expansion mechanism.
FIG. 3D shows the stent in an expanded state, with arrows showing the relative normal force.

FIGS. 3A-3D illustrate in cross-sectional view the forces applied to the tissue and anchoring system according to embodiments of the invention, and contrast these forces with those created by a device such as a stent that relies on expansion to achieve fixation. FIG. 3A shows the outer circumference of the foam 300 surrounding the sleeve in a tissue cavity 302 under normal pressure conditions. FIG. 3B shows the foam 304 and tissue 306 when negative pressure is applied. The application of negative pressure draws the tissue 306 toward the foam 304 until the tissue 306 and foam 304 are in contact. The foam 304 and remainder of the device are sufficiently pliable that the tissue 306 can compress the foam 304 and remainder of device during normal peristalsis of the GI tract. As shown in FIG. 2C, this can enable the tissue to contact the foam along the full surface of the foam, from the proximal portion of the anchoring mechanism 212 to the distal portion of the anchoring mechanism 214. The contact between the tissue and the foam results in a friction force the resists displacement of the device. The negative pressure causes the bowel to be pulled toward the sleeve, minimizing the ring tension applied to the tissue. This is important as expansile forces can create tissue stretching forces on the bowel wall that can cause stretch injury or decrease bowel wall perfusion. These issues are avoided using the device disclosed herein. The friction force is proportional to the normal force exerted on the device by the tissue and surface area of the foam interface. For the device according to some embodiments of the invention, the normal force is primarily determined by the negative pressure applied to the outer surface of the sleeve and the friction force is determined by the surface area of the sponge interface and characteristics of that sponge interface. These features will be described in more detail below.

In contrast, FIGS. 3C and 3D illustrate in cross-sectional view the forces for a stent-like anchoring device that relies on expansion to create friction. FIG. 3C shows the stent 308 in the bowel 310 prior to deployment of the expansion mechanism. FIG. 3D shows the stent 312 in an expanded state. The normal force in this case depends on the size of the bowel in relation to the size of the stent, and on the bowel's spring constant. The stent-like anchoring device uses expansive forces which are countered by the surrounding bowel. In order for the stent to achieve a similar normal force, and therefore a potentially similar anchoring force, as the device of the present invention, a high expansive force is required that results in much higher tension within the ring of tissue. A stent-like anchoring device to anchor must have a diameter greater than the diameter of the tissue cavity treated. Accordingly, the device according to some embodiments of the invention is capable of anchoring a sheath in the bowel with less stress and potentially less damage to the bowel tissue. Because the bowel wall is sucked down to the anchor using negative pressure in the disclosed device, the exact bowel size is less important than if the anchoring force depended on expansion forces employed by a stent or other expandable anchor types. Furthermore, the anchoring system can anchor in a tissue cavity at rest having a diameter that is greater than or equal to the diameter of the anchoring system. However, the anchoring system can also anchor in a tissue cavity having a diameter that is less than the diameter of the annular sealing mechanisms and/or the foam if the tissue cavity is stretchable.

Figure 4:
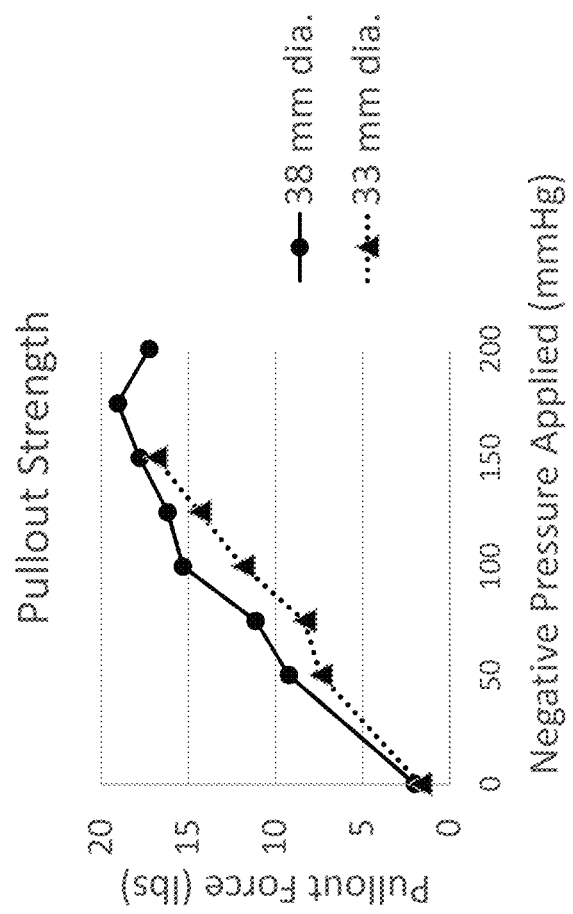
FIG. 4 shows data from pull-out strength testing of 38 mm and 33 mm in diameter configuration of the anchoring system at different levels of negative pressure.

FIG. 4 shows the pullout force as a function of negative pressure for devices according some embodiments of the invention. The pullout force is the force required to dislodge the device from a static state when negative pressure is being applied. For the purposes of this disclosure, this occurs when traction forces that mimic expulsion forces of the bowel are great enough to disrupt the sealing elements resulting in loss of anchoring or displacement of the device >1 cm down the length of bowel. FIG. 4 shows data for a device having annular sealing mechanisms with a 33 mm cross-sectional diameter, and a device having annular sealing mechanisms with a 38 mm cross sectional diameter.

The data in FIG. 4 demonstrate that with reduced diameter of the anchor portion of the device and associated reduced foam surface area there is some loss of anchoring strength. However, even with a much smaller diameter device, unlike a stent device that relies on expansion force for anchoring, a smaller diameter anchor still maintains high anchoring forces in the same size bowel lumen.

The pullout force is directly proportional to the pressure level delivered to the device and surface area of foam in contact with the bowel wall. Higher pressure will result in a higher normal force and resultant higher friction that resists pullout of device. The data in FIG. 4 demonstrate that large forces (>5 lbs) are required to dislodge the devices even when relatively small levels of negative pressure are applied. Negative pressure levels less than −200 mmHg have been shown to be safe to be used on human tissues, though perfusion is decreased at the area where negative pressure is delivered with increasing levels of negative pressure. A benefit of the device described herein is that even with relatively low levels of negative pressures around −100 mmHg, the anchoring system still resists a significant pullout force due to the friction created by the foam interface.

In addition, testing data demonstrates that even when the external diameter of the anchor device annular sealing mechanisms is in the range of about 50 percent the resting internal diameter of the bowel segment, anchoring can be effectively achieved. This is because when negative pressure is applied to the closed space of the intestine, the intestine can be sucked down to the device diameter. The ability of the device to anchor due to its design after negative pressure is applied in a tissue cavity much larger than the external diameter of the device allows the device to be placed in a lumen easily and without the need for subsequent expansion to achieve fixation within a cavity. A 65 mm in diameter segment of porcine intestine was used in benchtop testing model, and high levels (>5 lbs) of pullout strength was achieved with a 33 mm in diameter anchor at −75 mmHg and −150 mmHg. These data demonstrated an average pullout strength similar to smaller sizes of intestine tested with an average of 6.38 lbs and 12.62 lbs of force required for displacement for −75 mmHg and −150 mmHg of negative pressure, respectively. These data demonstrate that the bowel sucks down to the size of the anchor and the sealing elements form a seal even when the bowel is much larger in diameter than the anchor body. This is important as it allows for a small in external diameter anchor element to be placed into a segment of bowel without the need for expansion once the anchor element is positioned proximally within the bowel. The anchor element includes the sleeve, the annular sealing mechanisms on either side of the sleeve, the open-cell foam, and the pressure tube. This also allows for simplified delivery through an intestinal narrowing such as a stapled anastomosis which is typically significantly smaller than the natural resting bowel diameter. The device eliminates the need for an expansion mechanism such as a wire metal stent to achieve delivery of the device within a body cavity because a smaller in diameter device can be delivered through the bowel and still achieve the same or higher anchoring force. With the foam interface, the forces on the bowel are distributed across the entire contact surface area of the open-cell foam 120, further reducing the device's potential to damage the bowel.

Figure 5:
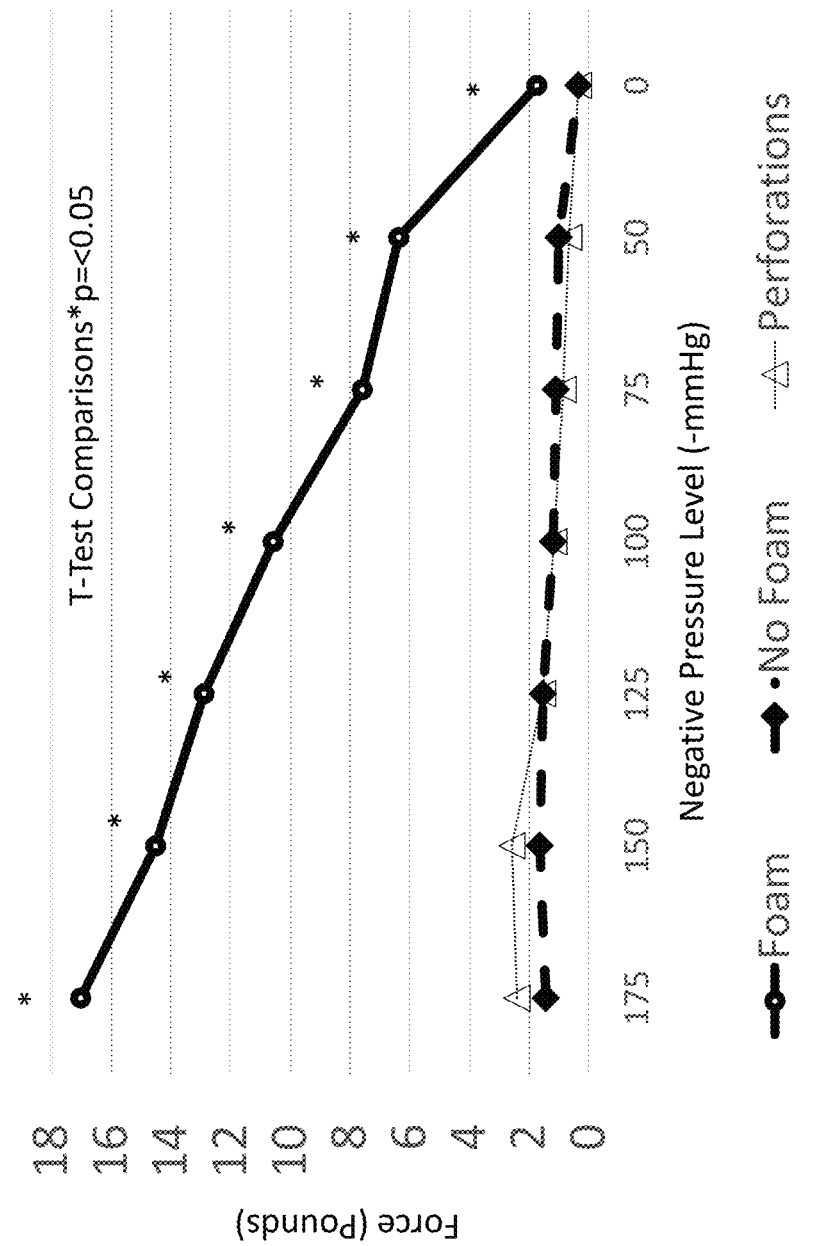
FIG. 5 shows pullout force for different configurations and pressures. T-test demonstrated significantly ($p=<0.05$) higher pull-out force for a 33 mm foam covered sleeve compared to a 33 mm sleeve without foam and a 33 mm sleeve with negative pressure suction through perforations and without foam.

FIG. 5 shows the pull-out force required to dislodge devices having three different configurations at various pressures. The three configurations include a sleeve with no foam, a sleeve with perforations and no foam, and a sleeve with foam. The configurations without a foam interface and with only perforations had significantly lower pull out strength (adhesion) compared to when the foam interface was utilized, as shown in FIG. 5. This is because the foam provides a uniquely large high friction surface area for the normal forces that result from negative pressure. These data are discussed in more detail below. Thus, having a foam interface or foam-like interface as part of the anchor device is an important element of the disclosed invention. Without open-cell foam, the device would not have the ability to anchor securely within the bowel lumen. For example, as tested and shown in FIG. 5, having a plurality of perforations or holes does not provide nearly the same anchor strength as foam. Furthermore, perforations or holes without a foam interface can suck tissue into the perforations or holes and result in areas of pressure injury, ischemia, and tissue damage. Because foam distributes pressure evenly over a large surface area, it prevents this type of injury from occurring.

Figure 18:
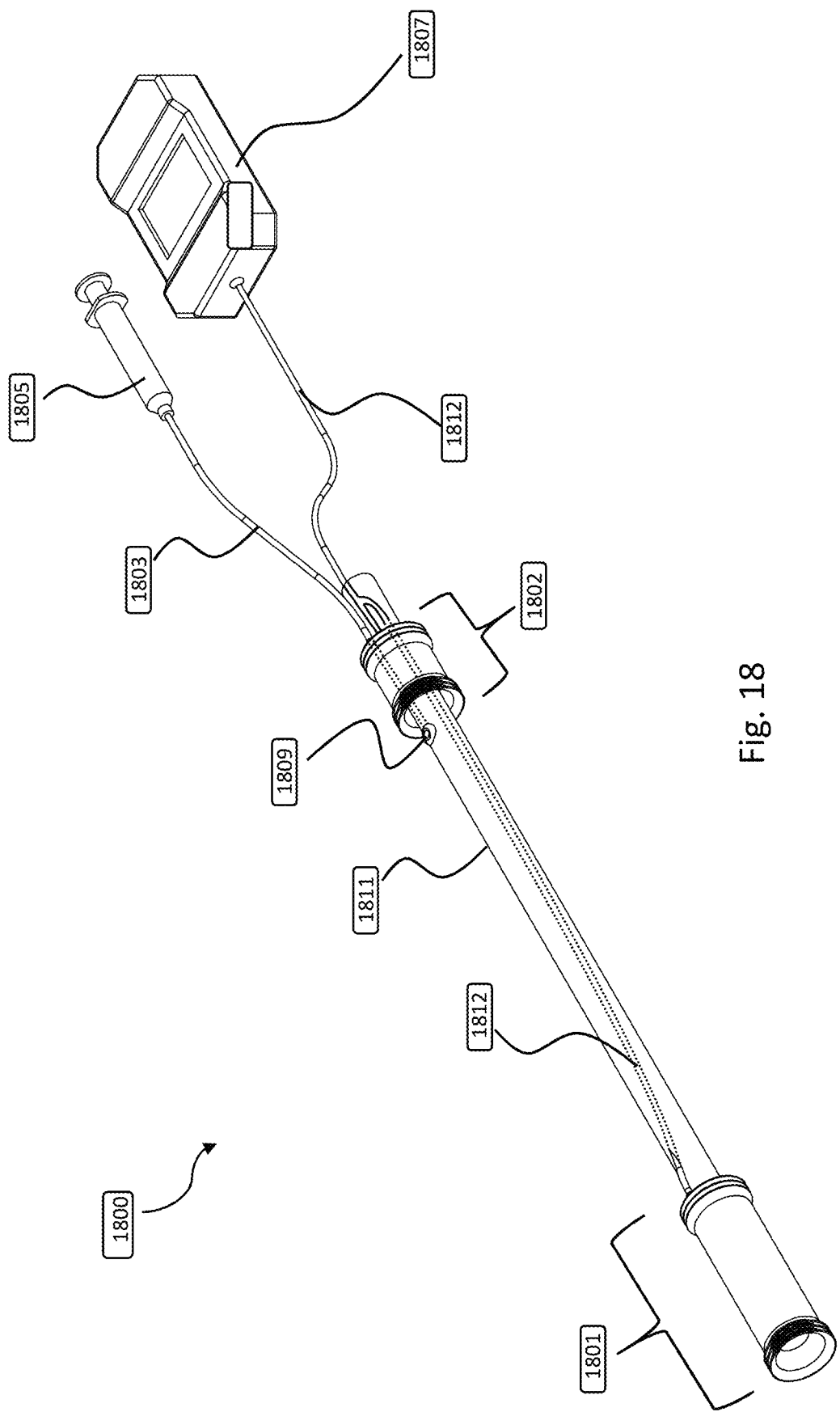
FIG. 18 shows an embodiment of the anchoring system that includes two anchor elements to deliver therapeutic agents to an isolated segment of bowel.
Figure 19:
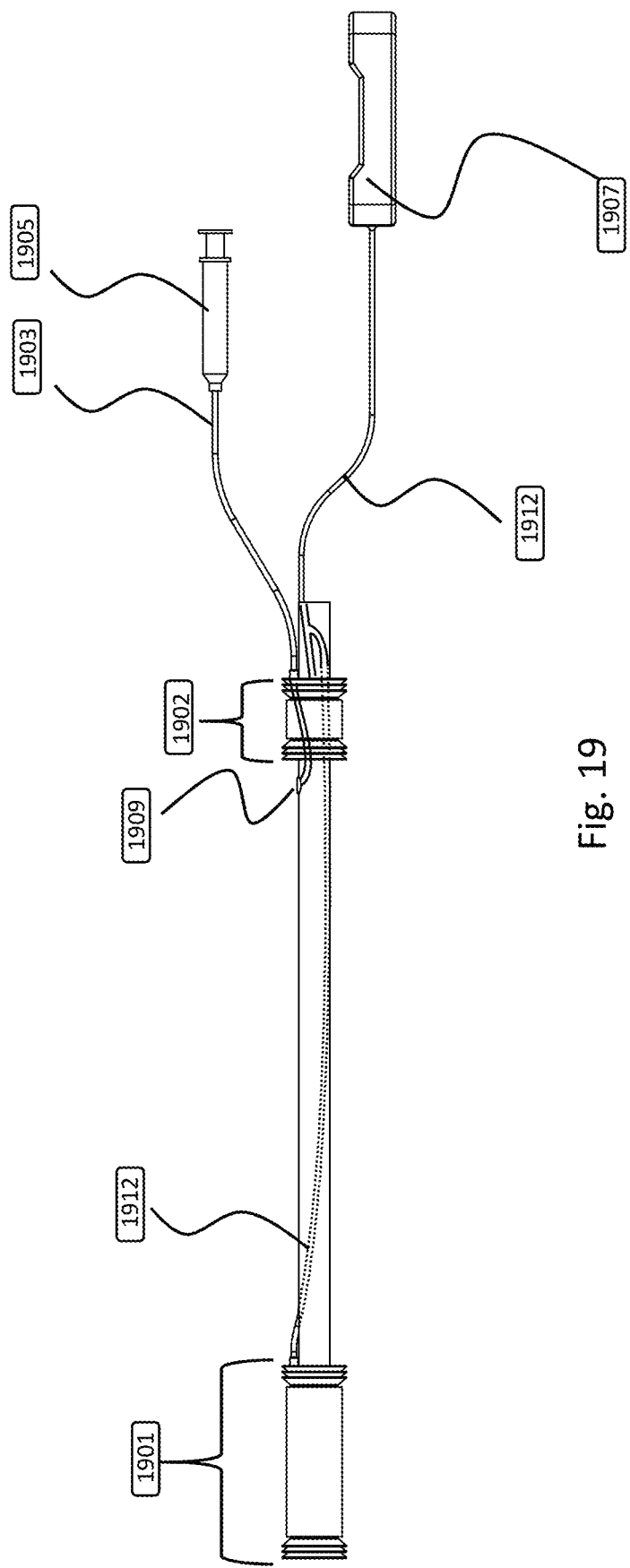
FIG. 19 shows a side view of an embodiment of the anchoring system that includes two anchor elements to deliver therapeutic agents to an isolated segment of bowel.

The anchoring system can be configured to have a series of anchoring configurations. In some embodiments, there is a single anchor element that includes the sleeve, a sealing mechanism on either side of the sleeve, foam, and pressure tubing. In other embodiments, the sheath may be anchored by a plurality of anchor elements. Besides increasing the anchoring strength, having two anchor elements is important for another embodiment of the device. FIGS. 18 and 19 show an anchoring system for treatment of the bowel wall. In this embodiment, the anchoring system 1800 has a first anchor element 1801 at the proximal end of the system that is placed proximally in the bowel to an area of bowel to be treated, and a second more distal anchor element 1802 that seals distally in the bowel beyond the area to be treated. There is a port 1809 in fluid communication with the sealed off space between the two anchor elements and between the bowel wall and external surface of the sheath where fluid can be introduced or removed. A fluid tubing 1803 in communication with the port 1809 can be used to introduce fluid from a fluid infiltration source 1805 such as a syringe. This port can be accessed from outside the patient's body via the fluid tubing 1803. This configuration of the device allows for delivery and removal of irrigation, drugs (such as antibiotics, anti-inflammatory drugs, or chemotherapy agents), and radiologic contrast between the external surface of the sheath 1811 and bowel wall between the two anchor elements 1801, 1802. In some embodiments, the second, more distal anchor element 1802 is shorter than the first more proximal anchor element 1801, since the anchoring force of the second anchor element does not need to be as strong and treatment near the anal verge may be required where a longer anchor element 1802 would not fit in the bowel. The system 1800 further includes a pressure tube 1812. The pressure tube 1812 can be in fluid connection with an outer surface of the sleeve of the first anchor element 1801 and the sleeve of the second anchor element 1802, as shown in FIG. 18. Alternatively, the system 1800 may include two pressure tubes, one for each of the first anchor element 1801 and the sleeve of the second anchor element 1802. The pressure tube 1812 is connected to a pneumatic system 1807 that is configured to apply negative pressure to the pressure tube to anchor the anchor elements 1801, 1802.

FIG. 19 is a side view of an embodiment of the double anchor element system, where like reference numerals as in FIG. 18 identify like features. This configuration is clinically important for a number of scenarios where treatment of an isolated segment of bowel could be beneficial. Because this configuration allows for controlled containment of a treatment agent within the bowel lumen for a discreet segment of bowel, this embodiment provides a unique ability to provide sustained and localized treatment of the bowel wall. For example, after endoscopic polypectomy, the excision site could be isolated with the disclosed embodiment and be treated with local chemotherapy. Another example might be inflammatory bowel disease, where an affected segment of bowel could have anti-inflammatory agents delivered and maintained at the site of disease. In cases of bowel wall damage or perforation, antimicrobial agents could be introduced to decrease bacterial load during healing and mitigate the risk of worsening infection. The two anchor elements can be spaced anywhere from about 1 cm to 6 feet depending on the indication and desired length of bowel to be treated. In some cases, the surgeon during and open case can advance the device manually from the outside of the bowel wall, so a very long segment of bowel could be treated and the upper limit is the length of the entire bowel. This applies to the one anchor element version of the device as well, as the device could potentially have a sheath length that could protect the entire bowel.

There are several key distinctions of this bowel protection device from negative pressure wound therapy treatment devices that may be used within the intestine. The disclosed anchoring portion of the device is not configured to treat an area of bowel injury, wound, or anastomosis directly. It is configured for anchoring a sheath portion of the device that protects the area of bowel injury, wound, or anastomosis. Importantly, the anchor portion of the device is designed to be positioned in healthy uninjured bowel above or proximal in the bowel from the area of bowel injury. This method dramatically increases the potential safety of this device as negative pressure is not delivered to the area of the anastomosis, damage or injury; thus, the protected area of bowel is never made ischemic or exposed to significant shear or traction forces from the device.

Negative pressure when delivered through a sponge interface to tissues has been shown to reduce the blood flow to areas where it is delivered. Thus, delivering negative pressure to the damaged area of the bowel itself can further damage the bowel or prevent healing as the blood supply of the bowel is less robust than for other tissues (especially at an area of anastomosis). Furthermore, the method and device described has a flexible sheath that covers the area of bowel anastomosis or damage; thus, the anchoring of the device is in a separate location than the area of damaged tissue. During bowel contraction at the area of damaged bowel, there are less mechanical forces exerted on the bowel when it constricts around the device because the flexible sheath is less mechanically rigid than a negative pressure wound therapy dressing that employ wire-stent based internal structures to maintain luminal patency and facilitate anchoring. In addition, by placing the anchor far away from the area of damaged bowel, the device does not exert mechanical force on the anastomosis or damaged tissue with traction or pulling on the device from the pressure tubing or other portions of the device that are external to the patient's body. No portion of the device is anchored distally to the damaged bowel; thus traction is only exerted on the proximal healthy bowel tissues. This further diminishes the risk of pulling apart an anastomosis repair or injuring further an area of damaged bowel.

Another difference is that the anchoring device described herein must have a much higher pullout strength as it must anchor strongly enough to maintain the entire sheath and anchor element in position in normally functioning, uninjured bowel. To accomplish this, the body has to be made long enough and wide enough to allow for adequate surface area of sponge contact to prevent expulsion, the anchor and sheath must be configured to conform to resist displacement by peristalsis, and the sealing mechanism must be made more robust to prevent potential air leaks.

Unlike a device that is designed to be mechanically dislodged by bowel function and peristalsis over time, the described device is designed to stay in place over an extended period of time until it is removed by the treating clinician. The higher anchoring strength of this anchoring system 100 and more solid fixation is important because it allows for placement of the device near the site of bowel being treated. In cases of bowel anastomosis in the colon, placement of a device higher into the bowel from the anus becomes more challenging due to the curvature of the bowel. So unlike devices that must be placed much higher (>40 cm above area to be treated) in the bowel due to device migration during the treatment period, the fixed anchoring provided by the disclosed anchoring system enables the anchoring element (sleeve, annular sealing mechanisms, and foam) to be placed only a couple of centimeters above the area to be treated. However, it may be preferable to have the anchor element placed at least 10 cm above the area to be treated to avoid local ischemia.

This ability to deliver controlled anchoring is achieved through the described design elements elaborated on below.

The components of the anchoring system according to some embodiments of the invention are described in detail below. Reference is made to FIG. 1 unless indicated otherwise.

Sleeve

According to some embodiments of the invention, the sleeve 102 is a flexible, concentric tube. The outer diameter and profile can be configured to move within the bowel without significant resistance when negative pressure is not being applied to the outer surface 114 of the sleeve 102. In some embodiments the external diameter of the sleeve is between 11 mm and 61 mm in cross-sectional external diameter. The internal diameter of the sleeve determines the diameter of the first lumen, and in some embodiments, the sleeve has an internal lumen diameter of between 10 mm and 60 mm in cross-sectional internal diameter. For anchoring in other tissue cavities than bowel, these parameters will differ based on the hollow viscus in which anchoring is to be achieved. In some embodiments, the sleeve may have a diameter that is greater than or equal to the diameter of the tissue cavity. In some embodiments, the sleeve may have a diameter that is less than the diameter of the tissue cavity. In some embodiments, the sleeve may have a diameter that is less than 95% of the diameter of the tissue cavity. In some embodiments, the sleeve may have a diameter that is less than 50% of the diameter of the tissue cavity. In some embodiments, the sleeve may have a diameter that is less than 25% of the diameter of the tissue cavity.

In some embodiments, the sleeve 102 is configured to be flexible enough to be easily removed by pulling on the sheath 116 to slide the sleeve 102 out through the bowel and anus, but rigid enough to hold a concentric shape so that it forms a lumen 106 when negative pressure is applied. This allows for easy placement and removal of the device 100. When negative pressure is applied to the outer surface 114 of the sleeve 102, the sleeve 102 and foam 120 surrounding the sleeve 102 conform to the contours of the GI tract.

The sleeve 102 is configured to be soft and pliable, and not to cause erosion into the bowel. The sleeve 102 has enough flexibility and compliance to allow for the proximal and distal ends of the sleeve to conform to the bowel contours so that the foam to bowel wall contact can be maintained during peristalsis and the annular sealing mechanisms 108, 110 can create and maintain a seal, yet keep the concentric tubular shape of the internal lumen 106 patent so GI contents can pass through. According to some embodiments, the sleeve 102 comprises medical grade silicone, polyurethane, thermoplastic elastomer, rubber, or other polymer exhibiting the flexibility and rigidity properties described herein. The flexibility of the sleeve 102 allows it to safely anchor in a patient's body because the flexibility of the sleeve reduces pressure points created from bowel contraction forces. The sleeve 102 according to some embodiments has a Shore A hardness between about 20 A and about 70 A to allow for maximum flexibility while maintaining a concentric form and patent lumen. The sleeve flexibility is also determined by the body wall thickness. The sleeve 102 is thin walled, again allowing for deformational forces to act upon it from bowel peristalsis. In some embodiments, the sleeve has a main body thickness of between 0.1 mm and 8 mm. The thinness allows for more durable materials to be utilized while continuing to accommodate peristaltic motion of the bowel wall.

The flexibility of the sleeve 102 allows the sleeve 102 to deform with the bowel during peristaltic motion. Peristaltic motion moves contents within the bowel by sequentially compressing the proximal section of bowel. FIG. 6A shows the anchoring system according to some embodiments of the invention anchored to the bowel wall 607 when the bowel is at rest. FIG. 6B shows the anchoring system during peristalsis. Arrows indicate the relative normal forces; larger arrows indicate larger normal forces and smaller arrows indicate smaller normal forces. Because the device is flexible it maintains a seal between the sealing mechanisms 608, 610, even with deformation by peristalsis or passage of enteric matter. It maintains surface contact between the foam 600 and bowel wall 607, and the bowel is able to compress the device without the device exerting large and potentially damaging forces on the bowel wall 607 in return. With constant negative pressure maintenance, the negative pressure between the sealing mechanisms 608, 610 creates nearer to constant normal forces during peristalsis along the length of the anchor element that prevents migration by maintaining the foam 600 to bowel wall 607 relationship. Accordingly, the device conforms and moves in conjunction with the bowel wall 607 because of the distribution of the adhesive forces over the entire surface of the sleeve covered by the foam interface.

The flexibility allows the sleeve to maintain the position of the foam 600 on the bowel wall 607 without creating shear forces between the foam 600 and bowel wall 607 during bowel contractions. In cases of less flexible bodies such as a stent-based anchor 612 in FIGS. 6C and 6D, the bowel is stretched and pulled around the anchor body because the anchor body cannot conform adequately to accommodate contractions occurring at or near the anchor body. These resultant shear forces disrupt the position of the device and can result in device migration. When the bowel contracts, the flexible sleeve deforms with the forces exerted through the attached foam so the foam can more easily deform with the bowel wall instead of shearing off the bowel wall resulting in device migration.

Furthermore, for a more flexible anchoring element, the peristaltic wave has less ability to push against the anchoring element due to the flexibility and conformity to the contraction. In cases of a more rigid and less conforming body such as a wire-based stent, the peristaltic wave has the resistance of the less deformable body to push against, resulting in device displacement.

Moreover, the flexibility, compressibility, and compliance of the disclosed device aids in placement and removal of the device through the curvature of the bowel lumen. The flexibility allows delivery of the device higher up in the digestive tract as the bowel becomes more tortuous and curved and allows for easy removal. This flexibility also allows for a longer sleeve 102 that has a larger foam 120 surface area and higher resultant anchoring strength to be manipulated into the bowel. This flexibility is also important for the anchoring system 100 as the foam 120 itself has a higher friction co-efficient than that of devices without foam, as shown in FIG. 5, even when no negative pressure is being delivered as during device removal and placement.

FIG. 5C shows a semi-rigid, stent-like device 612 in a bowel at rest, and FIG. 5D shows the stent-like device 612 during peristalsis. In contrast to the disclosed invention, the stent-like device 612 has a rigidity that resists compression. This rigidity increases the normal forces on the stent and the bowel as the bowel compresses, and causes the stent to slip along the surface of the bowel along with the peristaltic wave of normal bowel contraction. Some stent-based designs do have some compressibility and flexibility, but it is much lower than that of the disclosed device. Because of the low durometer construction, thinness, compressibility, and conformability of the device sleeve 102 according to some embodiments, the sleeve is much more resistant to displacement by peristaltic activity. The flexibility of the sleeve 102 and sealing mechanisms 608, 610 has the further advantage compared to more rigid devices of being more easily maneuvered for placement within the bowel along the normal longitudinal curvature of the bowel lumen. Moreover, when the device is placed in a region of bowel with longitudinal curvature, it is more easily able to conform to accommodate this curvature to maintain foam 600 to bowel surface area contact when negative pressure is applied and prevent pressure points that can potentially damage the bowel wall 607. In addition, the elimination of a wire-stent based structure greatly enhances manufacturability from both an ease and expense perspective.

The sleeve length determines the length of the anchoring element, and the length of the anchor portion of the device is also an important characteristic of the device. The anchoring strength of the anchor portion of the device is directly dependent on the length of the sleeve and associated surface area of the foam in contact with the bowel wall. Just like the diameter affects the surface area of the foam contact, so too does the length of the device. Unlike a stent, negative pressure dressing, or sheath that is located distally in the colon near the anal verge over an anastomotic site or area of damaged bowel that can be supported in place by the device rigidity and does not need to conform significantly to the bends of the intestine proximally in the bowel, the anchor portion of the system according to some embodiments is constructed in a window of lengths from >3 cm to <25 cm in length. Our testing in the porcine model indicates that if the anchor device is less than 3 cm in length with a diameter of 33 mm, it will not have the surface area to maintain a pull-out strength of >5 lbs and may be susceptible to loss of seal and low force device displacement (<5 lbs force). Furthermore, if the anchor portion of the device is longer than 25 cm in length, the device cannot easily be place around the anatomic bends of the intestine and positioned in the intended area of anchoring that is above (proximal in the bowel) the level of the area of bowel to be protected. For applications in other tissue cavities that require less pull out strength, such as a duct or esophagus, for example, the device may be shorter that 3 cm in length. Further, the embodiments of the invention are not limited to a flexible sleeve, and a stent-like sleeve surrounded in foam may also be used.

Sealing Mechanisms

The device 100 includes annular sealing mechanisms 108, 110 disposed at each end of the sleeve 102. The sealing mechanisms 108, 110 contact the inner surface of the tissue cavity in which the sleeve 102 is inserted. The sealing mechanisms 108, 110 serve at least two functions. First, they create the seals between the proximal and distal ends of the external surface of the sleeve 102 with the bowel wall to create the negative pressure space where the foam 120 can suck down to the bowel wall and create anchoring forces. Second, the seals create a fluid- and air-tight seal with the inner surface of the tissue cavity at either end of the sleeve 102 when negative pressure is applied to the outer surface 114 of the sleeve 102 that diverts GI content through the lumen 106 of the sleeve 102 and into the lumen 118 of the sheath 116 attached to the sleeve 102. The angle that the sealing mechanism's sealing elements are slanted minimizes the risk of fecal forward or back flow from causing disruption of the seal as fecal flow is directed towards the central lumen of the sleeve by the sealing element. In some embodiments, the angle of slant from perpendicular to the bowel wall is between 5 and 25 degrees. In some embodiments, the angle of slant from perpendicular to the bowel wall is 25 to 45 degrees. In some embodiments, the angle of slant from perpendicular to the bowel wall is 45 to 85 degrees. In some embodiments, there is no slant and the angle of slant from perpendicular to the bowel wall is 0 degrees.

The exact height of each sealing mechanism 108, 110 is less important than the relationship of the sealing mechanisms to the external diameter of the foam 120 covering. The sealing mechanisms 108, 110 of the system in some embodiments extend beyond the height of the foam 120 at rest so that when negative pressure is applied and the bowel wall collapses, a seal can be formed easily between the sealing mechanisms 108, 110 and bowel wall without interference by the foam 120. Thus, the annular diameter of the sealing elements is greater than the annular diameter of the foam dispersed on the body of the sleeve at rest when no negative pressure is applied. In some embodiments, the sealing mechanism 108, 110 extends at least 1 mm beyond the height of the foam 120 at rest.

The sealing mechanisms 108, 110 are made of a soft and flexible material that allows them to conform to the surface of the bowel. This is important because the peristaltic forces of bowel contraction can cause potentially harmful pressure points without this flexibility. For example, the sealing mechanisms 108, 110 can comprise thermoplastic elastomer, silicone, polyurethane, rubber, or other rubber-like materials or polymers. The Shore A hardness of the material can range between about 20 A and about 70 A. Similar to the low durometer of the sleeve, the low durometer of the sealing mechanisms allows for compression and conformation to the bowel lumen during the sealing process when negative pressure is applied and during bowel peristalsis. The conformability, flexibility, and compressibility of the sealing mechanisms 108, 110 in a similar fashion to the flexibility of the sleeve allow decreased displacement during peristalsis and easier device placement and removal.

The sealing mechanisms 108, 110 can include a plurality of sealing elements that are also referred to as fins or protrusions. Protrusions have a more rounded geometry and fins are have a more tapered geometry. Both protrusions and fins extend radially beyond the external diameter of the sleeve to form seals at each end of the sleeve. The sealing elements extend radially toward the inner surface of the tissue cavity to varying degrees. In some embodiments, the sealing elements extend beyond the foam radially allowing for sealing to occur at the ends of the sleeve 102 without interference from the foam 120. The sealing mechanisms 108, 110 may have multiple diameters along their body. Each sealing mechanism 108, 110 can be a single sealing element or divided into multiple sealing elements. A sealing element is a single annular air and fluid tight sealing protrusion. In the case of multiple sealing elements, the sealing mechanisms can be configured to conform to the GI tissue to create multiple local air and fluid tight seals. Some of the different sealing mechanism and sealing element embodiments are shown in FIGS. 1, 7A-7J, 8, 11, 12, and 14-16. According to some embodiments, the sealing mechanisms 108, 110 may be oriented in different directions and shapes to create specific surface areas where negative pressure is applied such as might be required for sealing in a hollow viscus other than the bowel with different anatomic geometry.

FIG. 7 shows some different configurations of sealing mechanisms and sealing elements in cross-section with only the upper half shown. FIG. 7A shows three sealing elements in series that are concentric protuberances oriented perpendicular to the sleeve. FIG. 7B shows three sealing elements in series that are concentric curved fins oriented perpendicular to the sleeve. FIG. 7C shows three sealing elements in series that are concentric protuberances oriented at about 25 degrees from perpendicular. FIG. 7D shows three sealing elements in series that are concentric curved fins oriented at about 25 degrees from perpendicular. FIG. 7E shows three sealing elements in series that are concentric protuberances oriented at about 45 degrees from perpendicular to the sleeve. FIG. 7F shows three sealing elements in series that are concentric curved fins oriented at about 45 degrees from perpendicular to the sleeve. FIG. 7G shows three sealing elements in series that are wider based concentric protuberances oriented perpendicular to the sleeve. FIG. 7H shows six sealing elements in series that are concentric, straight, and thin fins with a perpendicular orientation. FIG. 7I shows a single concentric curved fin sealing element that is oriented at about 45 degrees from perpendicular to the sleeve.

Figure 7A:
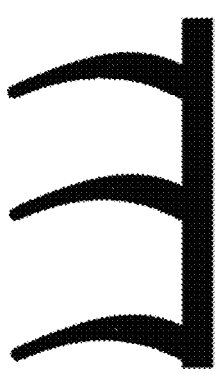
FIG. 7A shows a cross-section view of a first configuration of the sealing elements and sealing mechanisms.
Figure 7C:
FIG. 7C shows a cross-section view of a third configuration of the sealing elements and sealing mechanisms.
Figure 7E:
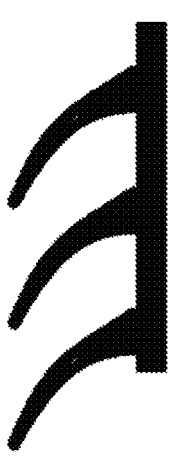
FIG. 7E shows a cross-section view of a fifth configuration of the sealing elements and sealing mechanisms.
Figure 7G:
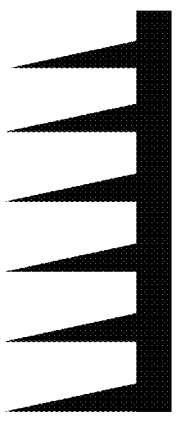
FIG. 7G shows a cross-section view of a seventh configuration of the sealing elements and sealing mechanisms.
Figure 7I:
FIG. 7I shows a cross-section view of a ninth configuration of the sealing elements and sealing mechanisms.
Figure 7B:
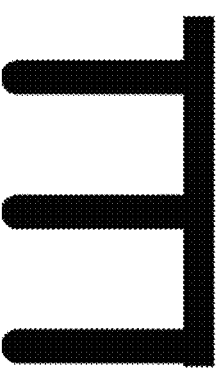
FIG. 7B shows a cross-section view of a second configuration of the sealing elements and sealing mechanisms.
Figure 7D:
FIG. 7D shows a cross-section view of a fourth configuration of the sealing elements and sealing mechanisms.
Figure 7F:
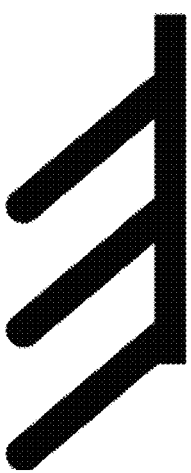
FIG. 7F shows a cross-section view of a sixth configuration of the sealing elements and sealing mechanism.
Figure 7H:
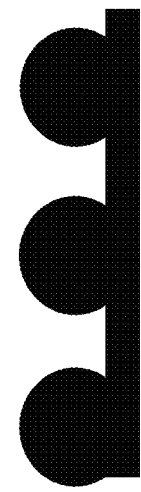
FIG. 7H shows a cross-section view of a eighth configuration of the sealing elements and sealing mechanisms.
Figure 7J:
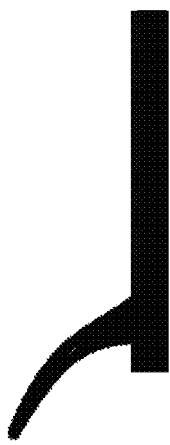
FIG. 7J shows a cross-section view of a tenth configuration of the sealing elements and sealing mechanisms.

FIG. 7J shows two sealing elements in series with concentric, straight, and thin fins oriented at about 60 degrees from perpendicular to the sleeve. According to some embodiments, the sealing elements have a contoured and tapered shape that becomes thinner as the distance from the sleeve 102 increases. These tapered fin shaped sealing elements as shown in FIGS. 7B, 7D, 7H, 7I, 7J, have several advantages. They reduce the stiffness of the outer portion of the sealing elements, thus reducing the possibility of bowel wall damage when negative pressure is applied. The combination of the low durometer material and thin tapered design allows for very little pressure to be placed on the bowel wall when negative pressure is activated. Also, the low durometer and thin tapered design allow for maximum flexibility to allow for conformation during bowel peristalsis. This helps to maintain the seal during deforming forces of bowel contraction and resists device expulsion. In some embodiments, the fins fold over to further mitigate bowel wall pressure points. The curved (FIGS. 7B, 7D, 7F and 7I), angled geometry (FIGS. 7C, 7D, 7E, 7F, 7I, and 7J), and asymmetrical triangular shape (7H) all help in orienting the sealing elements to fold in a direction away from the central portion of the sleeve 102 during negative pressure delivery and bowel wall compression. The sealing elements shown in FIGS. 7A-7J are non-limiting examples, and the embodiments of the invention are not limited to these configurations. Further, the sealing mechanisms may include two or more different types of sealing elements in a single sealing mechanism. Each sealing mechanism may have one or more sealing elements.

Figure 8:
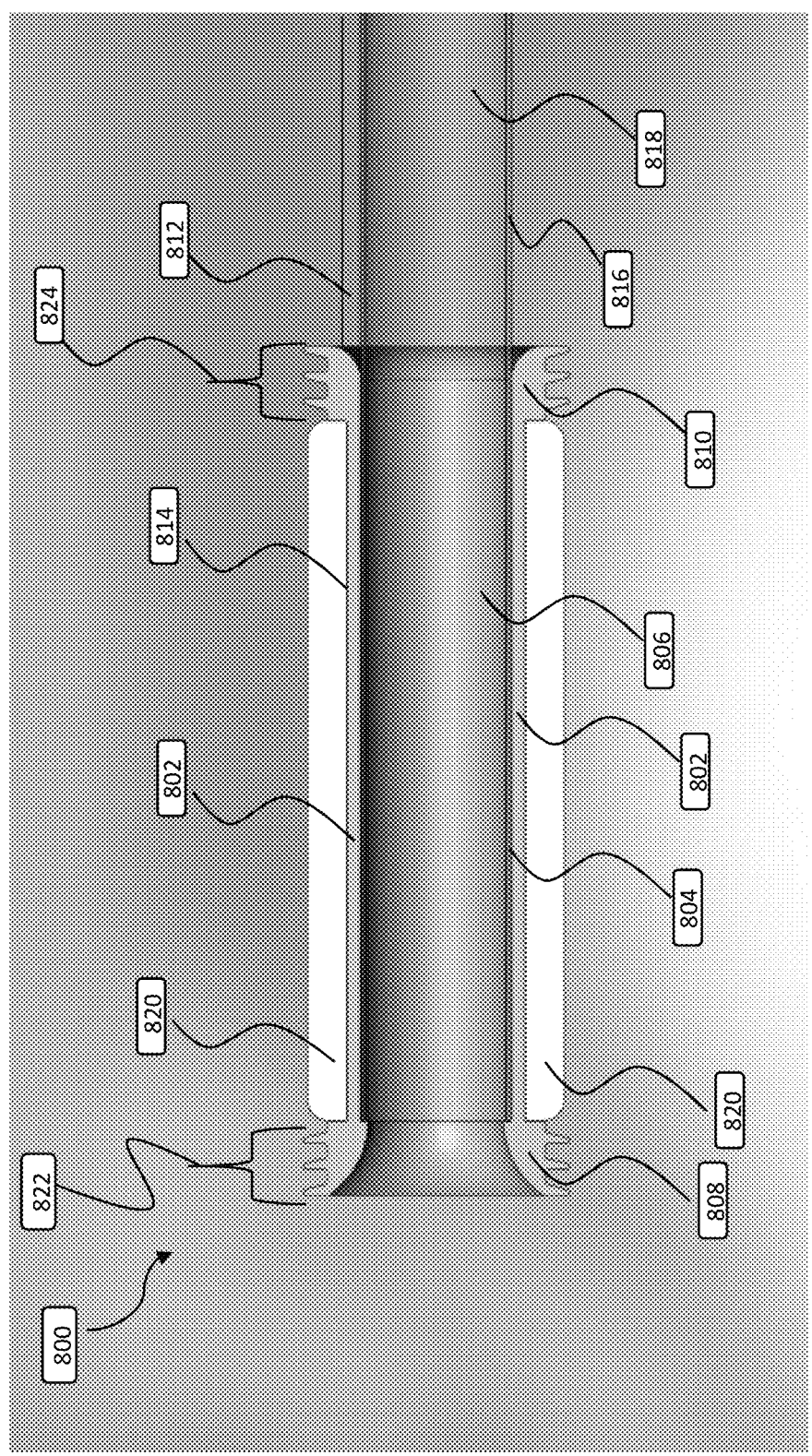
FIG. 8 shows a cross section of the anchoring portion of the anchoring system with an alternative sealing element geometry.

FIG. 8 shows an anchoring system 800 according to some embodiments of the invention, where like reference numerals as in FIG. 1 identify like features. The anchoring system 800 has sealing mechanisms 808, 810 having a plurality of fins 822, 824 according to some embodiments of the invention. Although the depicted fins 822 and 824 have angulations, angulation of the fins is not required if the fins are constructed of a soft enough material to conform to the bowel wall without significant pressure, but angulation of the fins can be beneficial. The angulation from perpendicular of the fins as shown in FIG. 8 is less than that of the fin embodiment shown in FIG. 1. Force of the bowel on the fins 822, 824 causes them to conform to the shape of the bowel. This establishes a seal with the surface of the bowel at each end of the sleeve 802, creating a vacuum chamber. The sealing elements conform to the walls of the tissue cavity, and reduce the pressure on any single point in the tissue cavity. Instead, the pressure is distributed over the length of the sealing element. The seals that create the vacuum chamber also prevent enteric material from flowing around the outside of the sleeve 802. The leading edge of the sealing mechanisms 808, 810 direct fluid into the lumen 806 of the sleeve 802 as the outer surface 814 of the sleeve 802 and the inner surface of the tissue cavity are brought closer together. In some embodiments, the sealing elements overlap, further reducing pressure points when sucked down to the bowel wall.

The sealing mechanisms according to some embodiments each have a plurality of sealing elements that are utilized at the ends of the anchoring portion of the device. These sealing elements create individual seals and provide redundancy of seals that increases the force required to displace the anchor when negative pressure is delivered between the seals. When traction or physiological intestinal expulsive force is placed on the anchor, the airtight seal formed between the device and the intestinal wall can be disrupted. When this occurs, the normal force and associated friction generated by the negative pressure suction is dissipated, resulting in decreased anchoring strength of the device. Having more than one seal has the advantage of providing redundancy when disruptive contractile (squeezing) peristaltic forces of the bowel, displacing forces from bowel contents, or traction forces are placed on the device.

Figure 9:
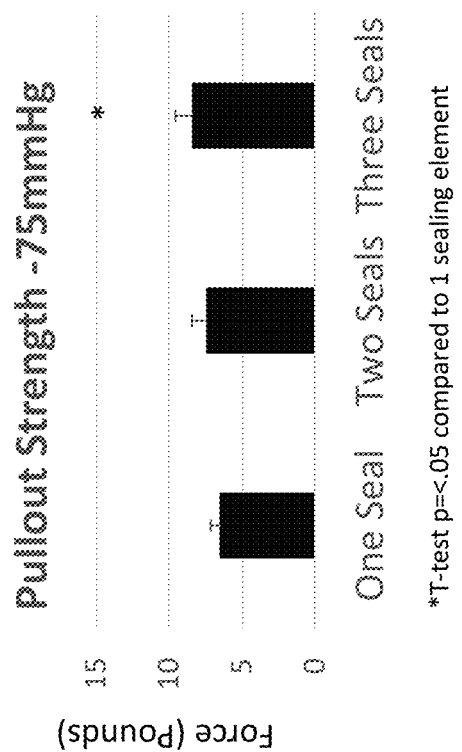
FIG. 9 shows data demonstrating pullout strength with one, two, or three sealing elements per side of the sleeve at −75 mmHg of negative pressure. The embodiment with three sealing elements has a significantly higher pullout strength than that with one sealing element.
Figure 10:
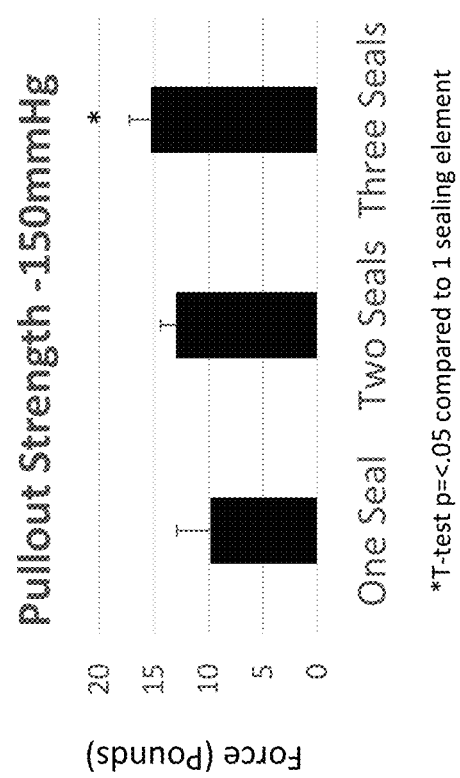
FIG. 10 shows data demonstrating pullout strength with one, two, or three sealing elements per side of the sleeve at −150 mmHg of negative pressure. The embodiment with three sealing elements has a significantly higher pullout strength than that with one sealing element.

We further demonstrated this using our pullout strength testing in a cadaveric porcine intestine model. The 33 mm anchoring device with foam was fashioned with one, two, or three sealing elements per sealing mechanism 108, 110 on each side of the sleeve. Pullout strength was measured by taking the force required to be placed on the device to achieve 1 cm of displacement (which was always accompanied by the loss of the suction seal) at −75 mmHg or −150 mmHg of negative pressure. FIGS. 9 and 10 show the pullout required for −75 mmHg of negative pressure and −150 mmHg of negative pressure, respectively. Pullout strength data for both levels of −75 mmHg and −150 mmHg of negative pressure demonstrated significantly ($p$-value≤0.05) higher pullout strength with three sealing elements versus one sealing element ($p$-value=0.0480 and $p$-value=0.0386). For example, for −75 mmHg of negative pressure, the force required to dislodge the device with one sealing element averaged 6.49 lbs, while the force required to dislodge the device with three sealing element averaged 8.38 lbs. For −150 mmHg of negative pressure, the force required to dislodge the device with one sealing element averaged 9.73 lbs, while the force required to dislodge the device with three sealing mechanisms averaged 15.21 lbs. These data provide support for the increased functionality of having multiple sealing elements (more than one per sealing mechanism) in a suction based intestinal anchoring system such as the one described here.

Figure 11:
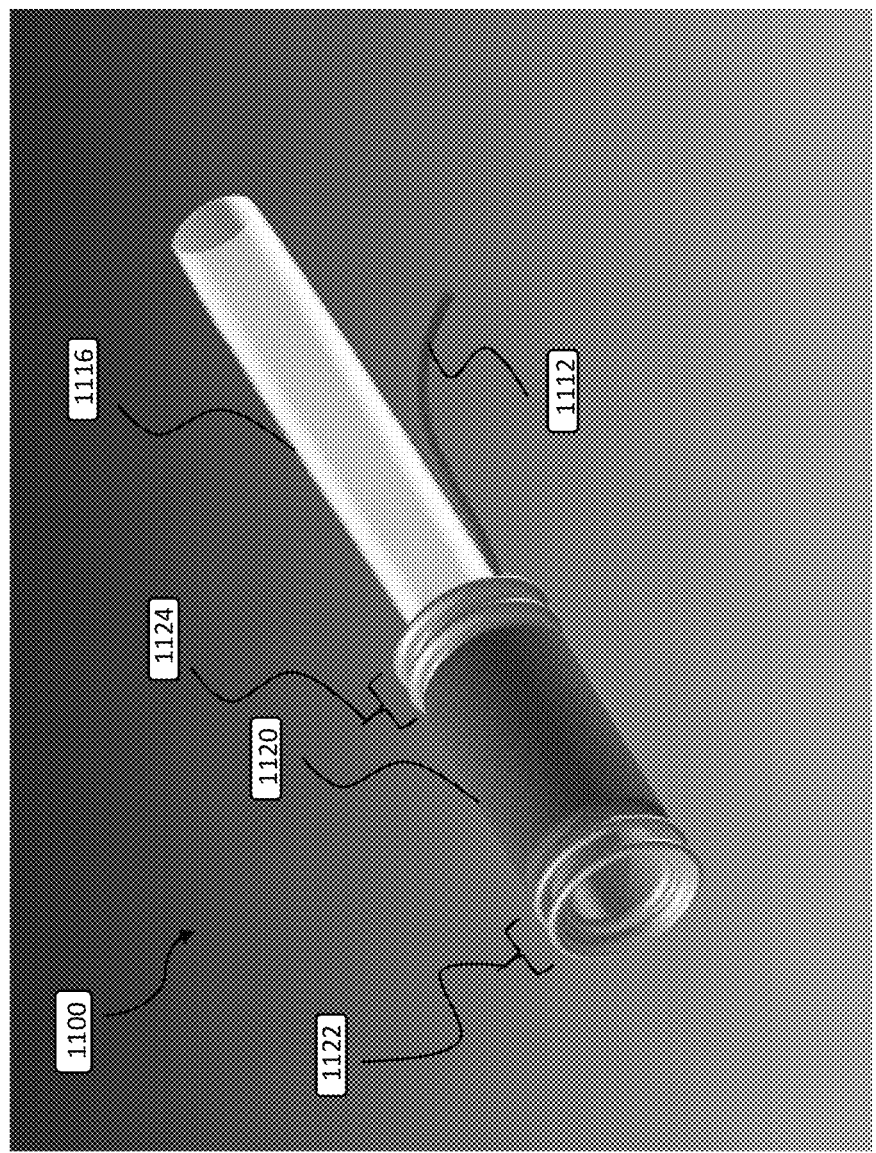
FIG. 11 illustrates an anchoring system according to some embodiments in which the sealing mechanisms have two sealing elements on each side of the sleeve that include concentric external protrusions that form a series of concentric seals.
Figure 12:
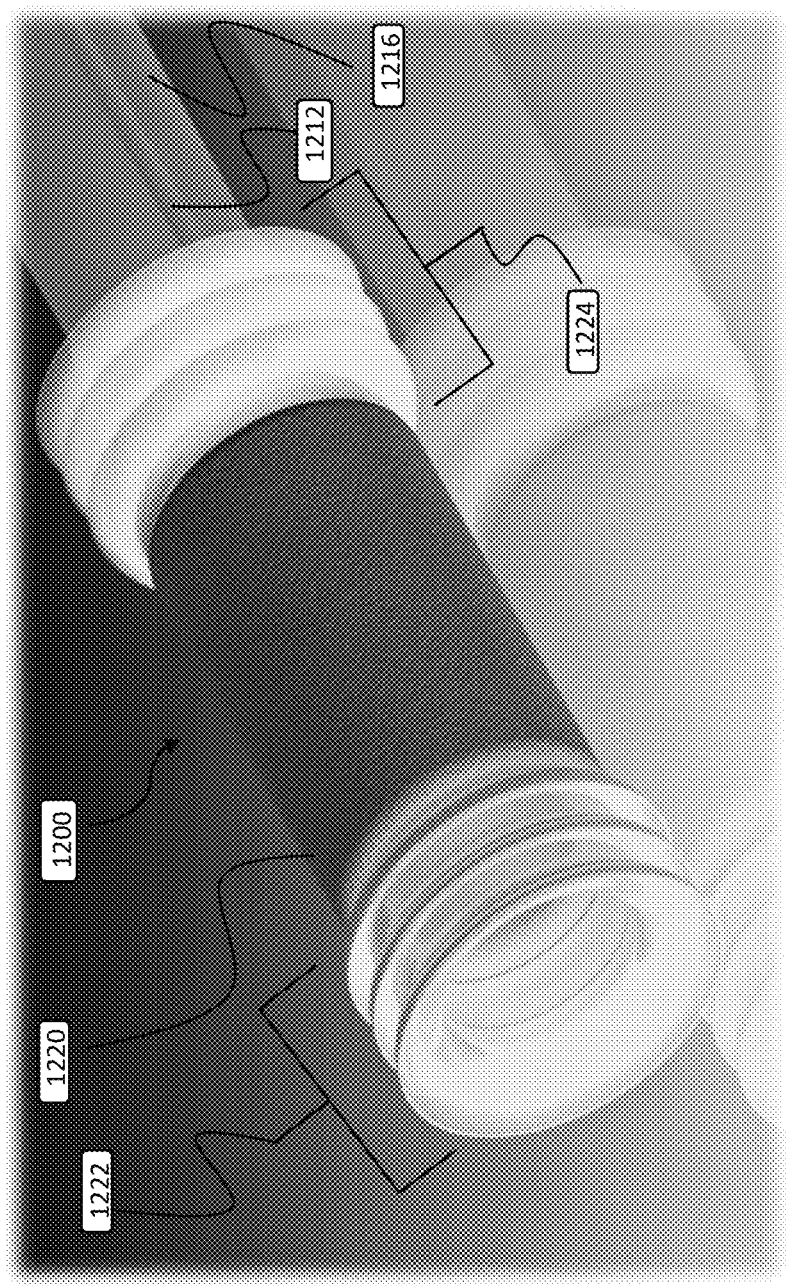
FIG. 12 illustrates an additional anchoring system according to some embodiments in which the sealing mechanisms have three sealing elements on each side of the sleeve that include concentric external fins that form a series of concentric seals.

FIGS. 11 and 12 illustrate some additional embodiments in which the sealing mechanisms are configured as concentric sealing elements that form a series of concentric seals. FIGS. 11 and 12 show anchoring systems 1100, 1200 according to some embodiments of the invention, where like reference numerals as in FIG. 8 identify like features. The sealing elements 1122, 1124, 1222, 1224 of these systems are configured to provide a series of seals to maintain a tight seal to the bowel even in the event of small amounts of leakage of air at a single seal. The sealing elements are configured to have a height and stiffness for forming an effective seal without causing pressure necrosis or erosion of the bowel wall as discussed above. In some embodiments, the plurality of sealing elements lay flat when sucked down to the bowel wall so as to not cause additional pressure points. This allows for significant pressure on the bowel only from the sealing elements actively maintaining the negative pressure seal. The embodiment shown in FIG. 11 is an embodiment that is configured with sealing elements 1122, 1124 as protrusions with rounded ends that have a small amount of angulation from perpendicular. The embodiment shown in FIG. 12 shows a device with sealing elements 1222, 1224 configured as thin-edged fins having more angulation from perpendicular than the sealing elements 1122, 1124 in FIG. 11.

The sealing mechanisms may be configured to be concentrically attached around the outer surface 114 of the sleeve 102 or may be integrated into the wall thickness of the sleeve 102. Specifically, this relates to the manufacturing process used to create the anchor, as the sealing elements may be made in one mold with the sleeve or they may be separately molded and adhered to the sleeve. According to some embodiments, the sealing elements and sleeve are created as a single molded part as both elements of the device have similar material property requirements of strength, flexibility, and conformability. In some embodiments, the sleeve 102 and sealing mechanism 108, 110 are made from a single mold using the same material.

In some embodiments, the sleeve is divided into multiple anchoring segments having an independent negative pressure supply. An anchoring segment is a section along the sleeve that independently anchors the sleeve. In one embodiment, the sleeve is divided by one or more additional sealing elements to create two or more sealed off areas along the sleeve that independently anchor to the bowel wall. Foam is placed between each sealed off section to distribute pressure and interface with the bowel wall. Negative pressure is applied to the spaces between the seals to create redundant areas of anchoring along the length of the sleeve. In some configurations, negative pressure is applied to each segment from independent negative pressure sources. In some configurations, the segments share the same negative pressure source. This embodiment, similar to having multiple anchoring elements, provides redundancy in the anchoring system. The advantage of this design is that if the seal is broken in one segment, there are still adhesive forces at another segment or segments.

Sheath and Collection Bag

The device 100 includes a sheath 116 that is in mechanical connection with the distal end of the sleeve 102. According to some embodiments, the sheath 116 is directly connected to the sleeve 102. According to some embodiments, the sheath 116 is indirectly connected to the sleeve 102. For example, the sheath 116 may be connected to the sealing mechanism 110 at the distal end of the sleeve 102. The sheath 116 forms a second lumen 118 that is in fluid connection with the first lumen 106. The sealing mechanisms 108, 110 divert GI content into the sleeve 102. When the GI content reaches the distal end of the sleeve 102 it enters the lumen 118 of the sheath 116. The sheath 116 can have a length that is sufficient to extend from the distal end of the sleeve 102 to a patient's anal canal, and outside the patient's body. Thus, once the GI content enters the sleeve 102, it is directed into the sheath 116, and is completely isolated from the inner surface of the patent's bowel distal to the sleeve 102. The sheath forms a barrier between the GI fecal flow content and the bowel wall, thereby protecting this portion of bowel. To isolate the bowel wall from fecal flow content, the sheath should be substantially fluid impermeable. Secondarily, the sheath also mechanically shields the bowel wall from mechanical expansion forces of GI flow contents.

According to some embodiments, the sheath 116 is bonded to the sleeve 102 or the distal sealing mechanism 110. The sheath 116 can have molded fixation attachments that are configured to lock into the sleeve 102 or the distal sealing mechanism 110. According to some embodiments, the sheath 116 is made of non-degradable biocompatible materials. For example, the sheath 116 can be made of silicone, polyurethane, thermoplastic elastomer, rubber, or other polymer, though the embodiments of the invention are not limited to these materials. The sheath should be substantially impermeable to fluid and bacteria.

The sheath 116 is configured so that its diameter allows it to dwell within the GI tract without obstructing the flow of GI flow material through it. In some embodiments, the sleeve has a cross-sectional diameter of between about 10 mm and about 60 mm. The sheath is made of an appropriate material and is thin and compliant enough so that the sheath is compressible by the bowel wall and does not eliminate the effects of peristaltic motion on fecal flow. Unlike a semi-rigid drainage tube designed primarily to maintain patency and depend on gravity and gastrointestinal flow pressures for movement of GI contents down the tube, the sheath according to some embodiments is deformable during peristalsis to allow for serial compressions to move GI contents down the sheath. This allows for placement of the device more proximally in the bowel, as gravity and GI flow pressure is inadequate to move material through a longer length of tubing because resistance to flow increases with tubing length. Furthermore, this compliance and associated flexibility allows for navigation around bowel curvatures, improves patient comfort, decreases the chance of bowel wall damage/erosion, and prevents sheath clogging. Some embodiments of the sheath 116 have a wall thickness of between about 50 microns and 5 mm. In some embodiments, the length of the sheath 116 is sufficient for it to extend beyond the GI tract out of the anal canal after device placement. In some embodiments, the sheath 116 is between about 8 inches and 72 inches in length. In some embodiments, the device is configured so that traction on the sheath 116 from outside the body can be used to remove the device from the body cavity. The sheath 116 must be strong enough to withstand longitudinal traction force without tearing of at least 10 lbs of force so that the sheath can be used to extract the sleeve after treatment is completed. The sheath 116 in some embodiments is marked with indicators along its length that show the length of sheath 116 residing inside of the GI tract or tissue cavity after placement in bowel or other tissue cavity. A user can use the indicators to determine whether the sleeve 102 is migrating. The sheath 116 according to some embodiments has a fixed length. According to some embodiments, the length of the sheath 116 can be adjusted by cutting the sheath 116.

According to some embodiments of the invention, a collection bag is disposed at the end of the sheath 116. The collection bag should be substantially impermeable to air and fluid. The collection bag collects GI content that flows through the sleeve 102 and the sheath 116. In some configurations, the sheath 116 ends in a port that can be kept closed for continence and opened to be emptied. In other configurations, the sheath 116 is flexible enough to allow the anal sphincter to compress the sleeve and provide continence. In this configuration a collection bag may not be used. According to some embodiments, the collection bag can be detached and replaced as needed. In some embodiments, the collection bag can be configured with a sealing attachment that allows for cutting of the length of the sleeve and re-establishing a seal to the bag. In some embodiments, the collection bag has markings such that the volume of effluence can be determined. In some embodiments, the collection bag has a leg strap for attaching the collection bag to the patient's body. In some embodiments, the collection bag can also contain a port to prevent any excess buildup of gasses. According to some embodiments, the external collection bag contains a one-way valve that prevents collected GI contents from flowing back into the sheath. In some embodiments, the collection bag has elastic leg straps that fasten the collection bag to the patient's body.

Foam

The device 100 includes foam 120 that is disposed on the outer surface 114 of the sleeve 102. The foam 120 or foam-like material serves a critical role in both increasing anchoring strength and preventing damage to the bowel. The foam 120 provides a critical friction force to hold the sleeve 102 in place when suction is applied to the outer surface 114 of the sleeve 102. In addition, the foam 120 distributes negative pressure and forces to minimize pressure points that might damage the bowel.

The foam 120 dispersed on the sleeve provides a high friction coefficient material with a maximum surface area where adhesion is created by the normal force created with negative pressure. Foam is the optimal material for distributing negative pressure in this application and providing an effective coefficient of friction when negative pressure is applied. One could envision a device that uses a membrane with a series of holes placed in close proximity to form a porous membrane to distribute negative pressure. However, the normal force generated by a membrane based device is limited by the open surface area created by the holes. In addition, the porous membrane has a much lower coefficient of friction than the rough surface of the foam. The foam also has a larger surface area of effective contact with the bowel due to its open cell structure and multiple pores for distributing negative pressure throughout its substance. To maintain a comparable pullout strength without foam, the magnitude of negative pressure required would have to increase and place significant point stresses on the bowel. This was demonstrated in a series of experiments performed in a cadaveric porcine intestine model as shown in FIG. 5.

FIG. 5 shows the results of testing the anchor pull out strength for a 33 mm diameter anchoring system 100 with various configurations. A 33 mm in diameter anchoring system 100 with foam 120 interface (the disclosed anchoring system), a 33 mm in diameter anchor device without foam 120 interface (the disclosed anchoring system with foam removed), and a 33 mm in diameter device with a plurality of perforations (a 33 mm in diameter anchor device with several dozen small 1-3 mm holes in communication with a negative pressure source via tubing) were inserted into porcine cadaveric intestine model and pullout force measurements were taken with various amounts of negative pressure delivered to the anchor. Pullout was defined as the amount of force required to dislodge the anchor with traction in the vector of the intestine. This force was measured as the maximum amount of applied force before the device lost its seal or was displaced by 1 cm. When the pullout force is reached, there is a drop in the force required to pull the device out of the intestine as the suction seal is broken or disrupted which also corresponds to the device displacing in the intestine. Each condition for each experiment was repeated three separate times. Trials were completed using the same segment of cadaveric intestine for each anchor, though different segments of intestine with slightly different diameter were used for repeat experiments. The data demonstrate that the anchor with foam had 4.5 to 14 times higher pullout strength than the anchor without foam. The data further demonstrate that the anchor with foam had a 5.6 to 12.2 times higher pullout strength than an anchor with a plurality of small suction perforations/holes. These results were dramatic and statistical analysis (one-sided, non-equal variance t-test) for each pressure demonstrate significantly higher pullout strengths at all pressures tested for the foam anchor compared to either of the non-foam anchors. The p-values demonstrating significant increased anchoring strength with foam compared to the anchor with foam removed were (175 mmHg) p-value=0.0012, (150 mmHg) p-value=0.0095, (125 mmHg) p-value=0.0079, (100 mmHg) p-value=0.0106, (75 mmHg) p-value=0.0034, (50 mmHg) p-value=0.0017, and (0 mmHg) p-value=0.0010. The p-values demonstrating significant increased anchoring strength with foam anchor compared to the anchor with surface of multiple holes/perforations were (175 mmHg) p-value=0.0003, (150 mmHg) p-value=0.0071, (125 mmHg) p-value=0.0071, (100 mmHg) p-value=0.0112, (75 mmHg) p-value=0.0042, (50 mmHg) p-value=0.0050, and (0 mmHg) p-value=0.0004. The anchor with foam removed and anchor with multiple holes did not exhibit statistically significant differences for pressure tested (all p-values >0.05). As these data demonstrate, the foam interface creates a significant increase in pullout strength and anchoring force at a given negative pressure suction level that is not achievable without foam 120 or foam-like substance. Even with multiple small perforations, pullout strength was only marginally increased when negative pressure was applied. In addition, with higher pressures, a multiplicity of perforation/holes design for suctioning to the bowel can potentially be dangerous as the areas of tissue sucked up into the holes can become ischemic as a continuous peripheral seal around each hole is necessary. In our cadaveric testing, we saw in the perforation model marking of the internal surface of the bowel where tissue was sucked into the holes of the anchor even with short duration of treatment used in these experiments. In contrast, the foam interface showed no internal surface marking. The open-cell foam 120 distributes the negative pressure evenly over the tissue better than individual holes or perforations and is much less susceptible to damaging bowel tissue. Foam 120 provides a distribution of the negative pressure forces that is uniquely both atraumatic to the intestinal tissues and creates high friction force that prevents the anchor from displacing.

The foam 120 comprises a material that is chosen to produce particular compression characteristics and coefficients of friction to prevent migration of the sleeve 102. The foam 120 can comprise a material having a pore size that allows negative pressure to be distributed throughout the foam, while preventing ingrowth of tissue into the foam. This allows the foam 120 to be easily dislodged from the inner surface of the tissue cavity when normal pressure is restored. In order to have the characteristics required to distribute negative pressure and create a high friction force, some embodiments of the foam 120 have an average foam pore size between about 50 microns to about 1000 microns in diameter. The average pore size of the foam in some embodiments is between about 100 and 300 microns. The average pore size of the foam 120 in some embodiments is between about 300 and 600 microns. Too small a poor size and the foam 120 loses some of its friction ability and too large a pore size and the material may have tissue ingrowth and has a lower tear strength. In some embodiments, the density and material composition of the foam 120 must allow for an overall tensile strength of the foam to be at least about 50 Kpa. This allows deforming forces and traction on the sleeve to not shear or tear the foam. Because the foam 120 is bearing the shear force exerted on the anchoring system 100 the foam must have a high tear force that can withstand about 50 Kpa of shear force and must be fixed to the sleeve 102 in a fashion that can withstand about 50 Kpa of distraction force without separation. The level of forces exerted on the device both from the peristaltic and expulsive forces on the sleeve 102 and sheath 116 are much higher than for keeping in place a piece of foam to treat a small wound area as might be done with negative pressure wound therapy.

The foam 120 in some embodiments is comprised of a material that is hydrophilic, which can prevent the foam from drying out the surface tissue with which it comes into contact, though a hydrophobic material can also be used in some embodiments. According to some embodiments, the foam 120 comprises polyvinyl alcohol. In some embodiments, the foam 120 is made of polyurethane, another polymer, or organic fiber mesh. In some embodiments, the open-cell foam 120 comprises a single tubular piece of foam.

The foam 120 covers the outer surface 114 of the sleeve 102, and creates a friction force when negative pressure is applied to the outer surface 114 that resists motion of the sleeve 102 with respect to the bowel. The porosity of the foam 120 allows air to be evacuated from the region between the outer surface 114 of the sleeve 102 and the inner surface of the tissue without strong suction being applied to any single point. This creates a frictional force that is evenly distributed across the outer surface of the foam 120. The foam 120 under negative pressure also creates a large surface area where frictional forces are created to resist dislodgement. The foam 120 is designed to be compressible to minimize the amount of force exerted on any single point of the bowel when negative pressure is applied, and to maximize the surface area contact to the bowel wall by conforming to the shape of the bowel wall.

In some embodiments, the foam 120 dispersed over the sleeve must have a thickness or height that allows for dispersion of negative pressure around the sleeve but does not extend beyond the height of the radial edge of the sealing mechanisms at rest or results in narrowing of the sleeve lumen 106 to the point of obstructing GI content flow. If the foam 120 is too thin, it will collapse or clog and not have enough open pores to evenly distribute negative pressure around the sleeve 102. If the foam is too thick, it will prevent air tight seals from initiating at the sealing mechanisms 108, 110 and constrict the diameter of the sleeve lumen 106. In some embodiments the thickness of the foam disposed around the sleeve is between 2 mm and 1.5 cm.

According to some embodiments, the foam 120 can be segmented into separate subunits. In some embodiments, multiple pieces of foam are dispersed around each anchoring segment. As described above, these segments can be separated by multiple serial sealing elements. In these embodiments, negative pressure can be applied to all of the subunits in parallel or separately through independent negative pressure supplies.

Alternatives to foam may be used in some embodiments of the disclosed invention to form the interface with the bowel wall. These foam-like alternatives must distribute negative pressure evenly through the material, create a significant friction force to resist displacement when negative pressure is applied, have biocompatibility with the tissues of the GI tract, and compressibility and deformational properties that resist expulsion and pressure induced tissue damage. Some potential polymer-based alternatives are stacked mesh matrices that are wrapped around the sleeve, a honey-comb lattice of interconnected channels oriented in a radial fashion around the sleeve, or 3-D woven synthetic fabric material. Natural fiber alternatives include guaze, naturally occurring sponges, or woven fabric. However, some embodiments of this device utilize open-cell reticulated foam.

Pneumatic System

The device 100 includes a pressure tube 112 that is in fluid connection with the outer surface 114 of the sleeve 102. The pressure tube 112 is connected to a negative pressure source such as an air pump that sucks air out of the tube in a controlled fashion. This pump maintains constant negative pressure at a level of pressure that allows for adequate anchoring so that the sleeve does not become dislodged, but does not harm the bowel. The configuration of device allows for physiologically safe pressures of up to −200 mmHg, though pressures of −50 to −150 mmHg may be the preferred range of negative pressure delivery. When negative pressure is applied to the tube, a seal is formed by the sealing mechanisms 108, 110 at either end of the sleeve 102. As the pressure tube 112 connected to a negative pressure source continues to apply negative pressure, the inner walls of the tissue cavity are pulled toward the outer surface 114 of the sleeve 102, bringing the tissue into contact with the sealing mechanisms 108, 110 and the foam 120. The normal force created by the negative pressure sucking down the foam creates a friction force that resists motion of the sleeve 102. The pressure tube is configured to resist occlusion from wall collapse when negative pressure is applied. In some embodiments, there are more than one pressure tubes to provide redundancy in case of kinking or clogging of any one pressure tube. In some embodiments with a plurality of pressure tubes, more flexible and compliant tubing material can be utilized due to the redundancy of negative pressure delivery. Each of these pressure tubes are individually in fluid communication with the foam to allow for negative pressure delivery. In some embodiments, where there are multiple anchoring elements or in cases where there are multiple anchoring segments, there may be separate pressure tubes to each anchoring element or anchoring segment. The plurality of pressure tubes can be connected to a single negative pressure source such as a single pump or individually to a plurality of pressure sources such as multiple pumps.

The pressure tube 112 extends from the sleeve 102 beyond the anus. The pressure tube 112 can be disposed within the wall of the sheath 116 or be separate. According to some embodiments, the sheath 116 defines an additional lumen in which the pressure tube 112 is disposed such that it is isolated from the GI content traveling through the sheath. Alternatively, the pressure tube 112 can be situated alongside the sheath 116, either attached to the outside of the sheath 116, inside the sheath 116, or detached from the sheath 116. In another embodiment, the additional lumen in the sheath is the pressure tube.

Figure 13C:
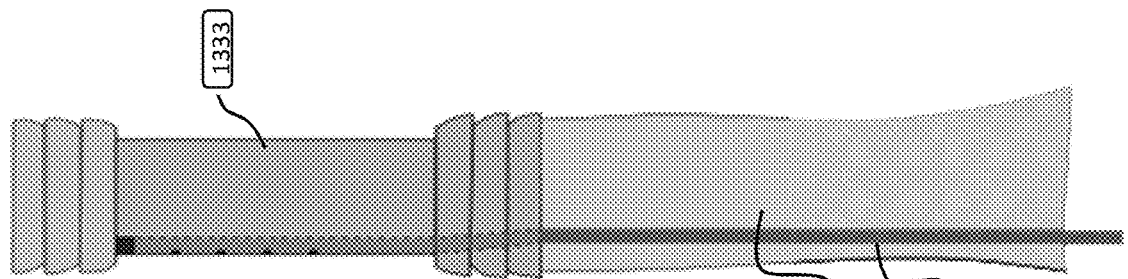
FIG. 13C illustrates a third configuration of the junction between the sleeve and the pressure tube according to some embodiments.
Figure 13B:
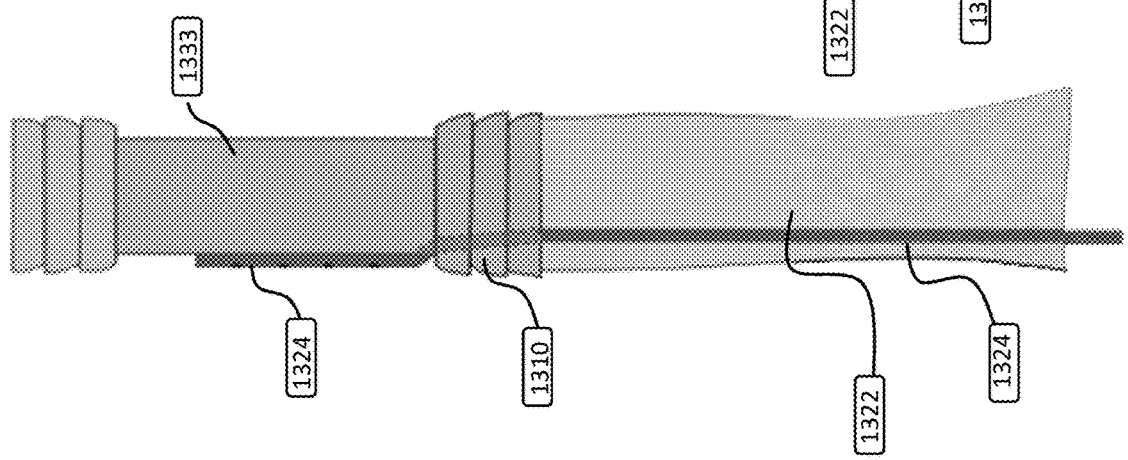
FIG. 13B illustrates a second configuration of the junction between the sleeve and the pressure tube according to some embodiments.
Figure 13A:
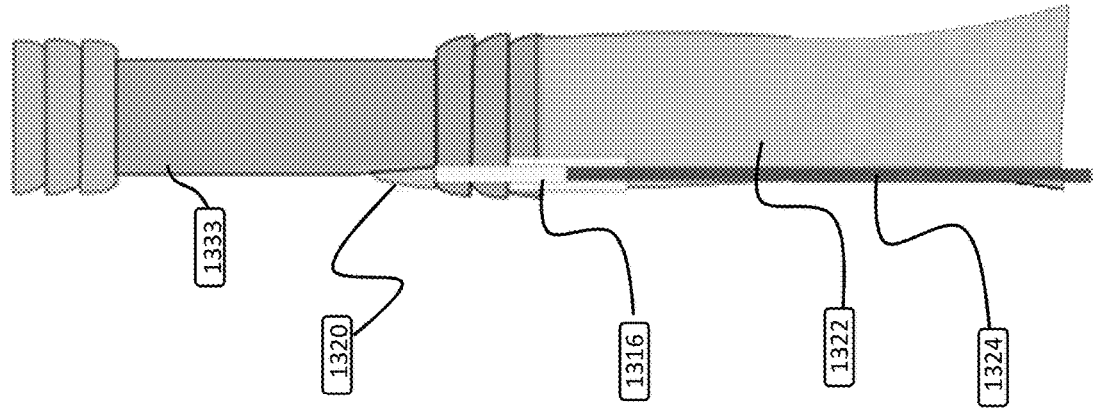
FIG. 13A illustrates a first configuration of the junction between the sleeve and the pressure tube according to some embodiments.

The proximal end of the pressure tube 112 can be connect to the distal end of the sleeve 102 or to the annular sealing mechanism 110 disposed at the distal end of the sleeve 102. FIGS. 13A-13C illustrate configurations of the pressure tube 1324 and sleeve 1333 according to some embodiments of the invention. The foam is not shown in FIG. 13A-13C so that the relationship between the sleeve 1333 and the pressure tube 1324 can be shown more clearly. In some embodiments, the outer surface of the sleeve 1133 including the openings in or to the pressure tube will be covered in open-cell foam.

FIG. 13A shows an embodiment in which the sleeve has a tube-like feature 1316 that protrudes from the distal end of the sleeve 1333 and is open to the outer surface 1320 of the sleeve 1333. The end of the tube-like feature 1316 is sized to connect to the proximal end of the pressure tube. The two parts are bonded or welded together to create an air and fluid tight seal.

FIG. 13B illustrates an embodiment in which the pressure tube 1324 runs through a secondary lumen of the sheath 1322. A hole is punched through the side of the distal annular sealing mechanism 1310 or sleeve 1333, and the pressure tube 1324 is routed through to the outer surface of the sleeve under the foam (not shown). Multiple holes are punched into the pressure tube to create redundant pathways for negative pressure delivery and to prevent clogging from disrupting negative pressure delivery. A sealant/adhesive is used to bond the pressure tube to the sleeve, and to create an air tight seal around the pressure tube where the hole was punched in the annular sealing mechanism 1310 or sleeve 1333.

FIG. 13C illustrates an embodiment where the pressure tube 1324 is routed straight through the secondary lumen of the sheath 1322 and into the inner lumen the sleeve 1333. According to some embodiments, the pressure tube 1324 extends to the proximal end of the sleeve 1333. An adhesive may be applied to the pressure tube 1324 to hold it in place against the inner surface of the sleeve 1333. The proximal end of the pressure tube 1324 is sealed. Holes are punched along the length of the sleeve 1333 through the sleeve and into the pressure tube 1324 to create communication between the outer surface of the sleeve 1333 and the pressure tube 1324 and negative pressure source. Foam (not shown) is disposed on the outer surface of the sleeve 1333 so that the pressure is distributed over the surface of the foam, instead of being concentrated at the holes in the sleeve 1333.

Figure 14:
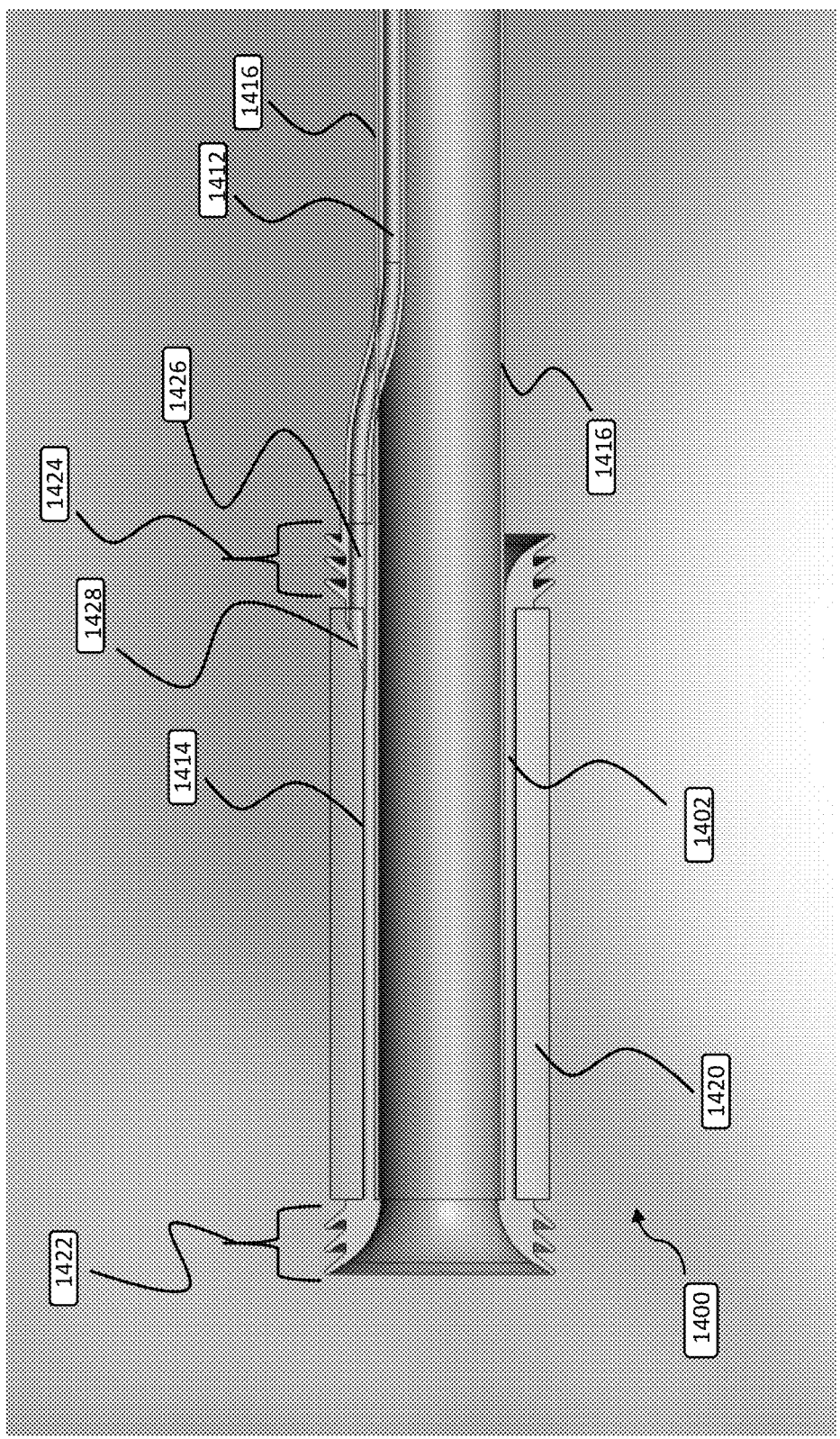
FIG. 14 shows a side cross-section view of an anchoring system according to some embodiments of the invention.
Figure 15:
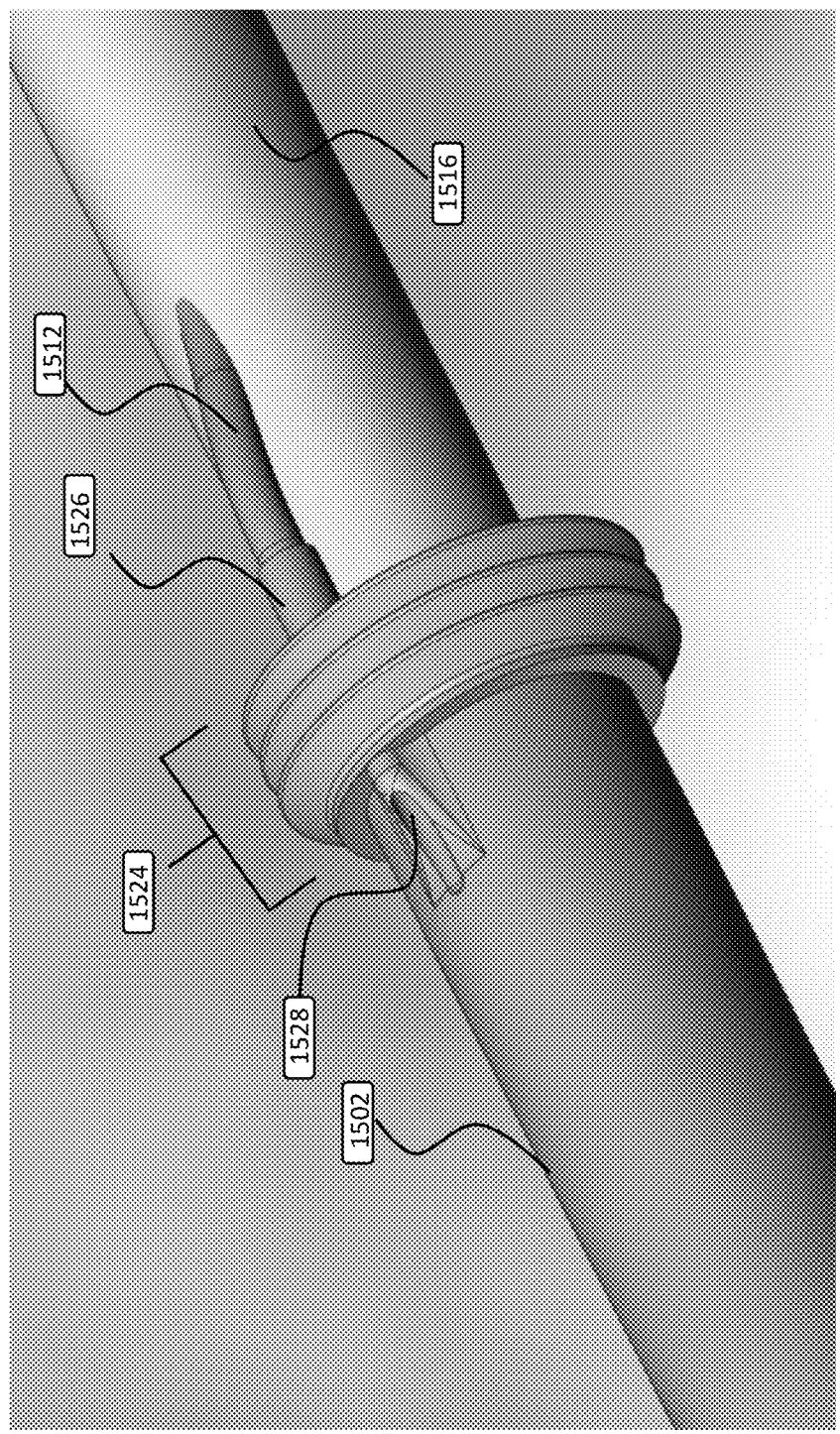
FIG. 15 shows a junction between the sleeve and the pressure tube according to some embodiments.

FIG. 14 shows a cross-sectional side view of an embodiment of the anchoring system 1400 corresponding to the device shown in FIG. 13A, where like reference numerals as in FIG. 1 and FIG. 8 identify like features. The tube-like feature 1426 connects the pressure tubing 1412 to the outer surface 1414 of the sleeve 1402 through an opening 1428. FIG. 15 shows a close-up view of the integration of the pressure tube 1512 with the annular sealing mechanism 1524 and the sleeve 1502. As described above with reference to FIG. 13A, the sleeve has a tube-like feature 1526 that protrudes from the distal end of the sleeve and connects to an opening 1528 on the outer surface of the sleeve 1502. The tube-like feature 1526 enables the pressure tube 1512 to be coupled to the outer surface of the sleeve 1502 without disrupting the sealing function of the sealing mechanism 1524. The proximal end of the tube-like features is open so that negative pressure can be delivered to the outer surface of the sleeve 1502 and foam (1420 in FIG. 14, not shown in FIG. 15).

Figure 16:
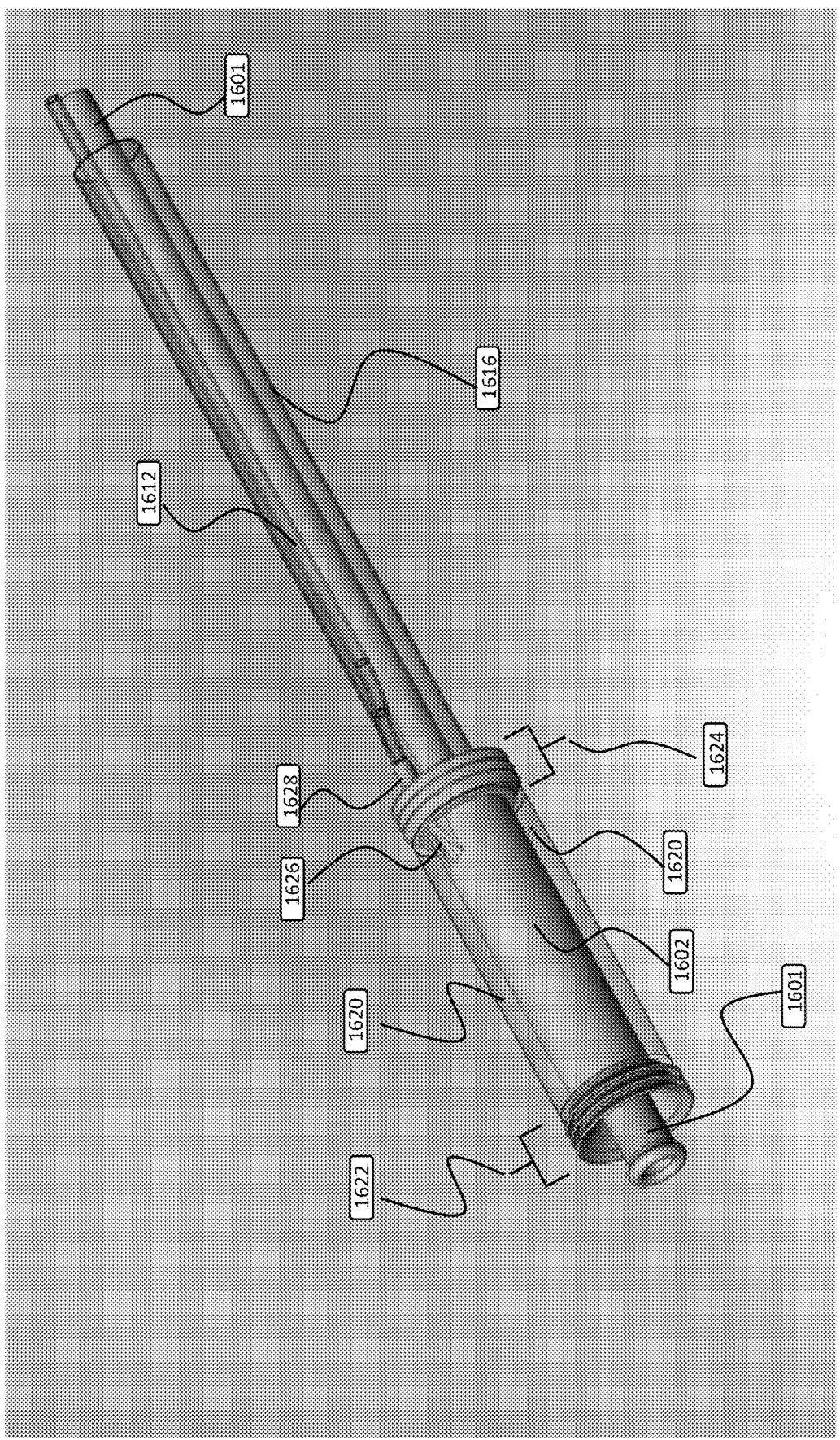
FIG. 16 illustrates an anchoring system with a deployment device disposed in the lumen of the sleeve and sheath.

FIG. 16 is a zoomed-out view of an anchoring system having the tube-like feature shown in FIGS. 14 and 15. The anchoring system is shown with a semi-rigid tube pusher 1601 disposed in the lumen of the sleeve 1602 and sheath 1616. The tube-like feature 1628 is connected to the pressure tube 1612 that has an opening 1626 to the outside surface of the sleeve 1602. Foam 1620 is dispersed around the sleeve 1620 between the proximal and distal annular sealing mechanisms 1622, 1624 and covers the opening 1626 of the tube-like feature 1628.

According to some embodiments, the sleeve 102 and/or the second annular sealing member 110 has a nozzle connected to the pressure tube 112 in continuity with the space occupied by the foam 120 that is configured to be low profile and not impede flow through the lumen of the sleeve 102. According to some embodiments, the pneumatic interface contains a one-way valve that maintains the pressure gradient during momentary loss of negative pressure delivery from the pneumatic device. The one-way valve can be disposed in the tube-like junction shown in FIGS. 13A, 14, and 16, or in the interface between the pressure tube and the vacuum source. According to some embodiments, an additional lumen in the sheath 116 is the pressure tube 112, and ports connecting to the additional lumen may contain 1-way valves which are oriented to prevent the loss of suction. In some embodiments, these are one-way duck bill valves.

According to some embodiments, the pressure tube 112 is part of a pneumatic system that controls the pressure on the outer surface 114 of the sleeve 102. The pneumatic system includes a pump that pulls air out of the pressure tube 112 and maintains near constant negative pressure at a set pressure level in the range of −50 mmHg to −200 mmHg. The pneumatic pump may also in some configurations be capable of applying positive pressure, for example to assist in removal of the sleeve 102 from the patient's bowel. The pneumatic pump can maintain negative pressure through an electric pump mechanism or mechanical pump mechanism. The pneumatic system may include an indicator that allows the user to determine whether sufficient negative pressure has been achieved and maintained. For example, the pressure gauge can be an indicator that demonstrates that sealing is maintained as suction force is measured within the pneumatic system.

In some embodiments, the pressure tube 112 has an adaptor that can be used to attach a syringe so that the pressure tube can be flushed and the foam 120 irrigated with fluid. This can be helpful with removal of the device from the bowel wall during the removal procedure or for flushing GI contents away from the foam interface that might clog the pneumatic system.

Insertion and Removal

During insertion into a patient's bowel, the device 100 is introduced into the anal canal and moved past the anastomosis site, so that the annular sealing mechanism 110 disposed at the distal end of the sleeve 102 is proximal to the anastomosis. The method of deployment depends on the level of the anastomosis. For low anastomosis, the device can be deployed through a capsule sheath system that is positioned manually. For higher anastomosis, an endoscope can be used to assist in the deployment. The device can be placed over the outside of an endoscope and affixed such that a user can position and deploy the device in the desired location.

According to some embodiments, the anchoring system 100 is configured to be placed into position by an endoscope. The device 100 can have a suture or tab present that can be grasped by an endoscope grasper to pull the sleeve 102 in place using an endoscope. In some embodiments, the device is attached to a releasable clip on the end of the endoscope that can release the device from the end of endoscope from outside the body. Alternatively, an endoscope may be used to hold a flexible member such as a wire or string attached to the anchor that is looped out of the patient's body and pulled around the fixed end of the endoscope within the bowel to pull the device into the bowel and into the desired position.

In some embodiments, the sleeve 102 can be attached to the endoscope using a releasable from outside the body clamping mechanism. In some embodiments, the sleeve 102 can be attached to semi-rigid tubing that fits over the endoscope. This tubing is configured to push the anchoring system 100 into place over the endoscope and then to release from the anchoring system 100. In other embodiments, the introducing member is a first semi-rigid tube that contains the proximal portion of device. This first semi-rigid tube is advanced into the bowel through the anus, and after reaching the desired position, a second semi-rigid pushing tube that encircles the sheath and is smaller in diameter than the first semi-rigid tube is used to hold the device in place while the first semi-rigid tube is removed. The second semi-rigid pushing tube is then removed after negative pressure anchoring of the anchoring system 100 is initiated.

Figure 17:
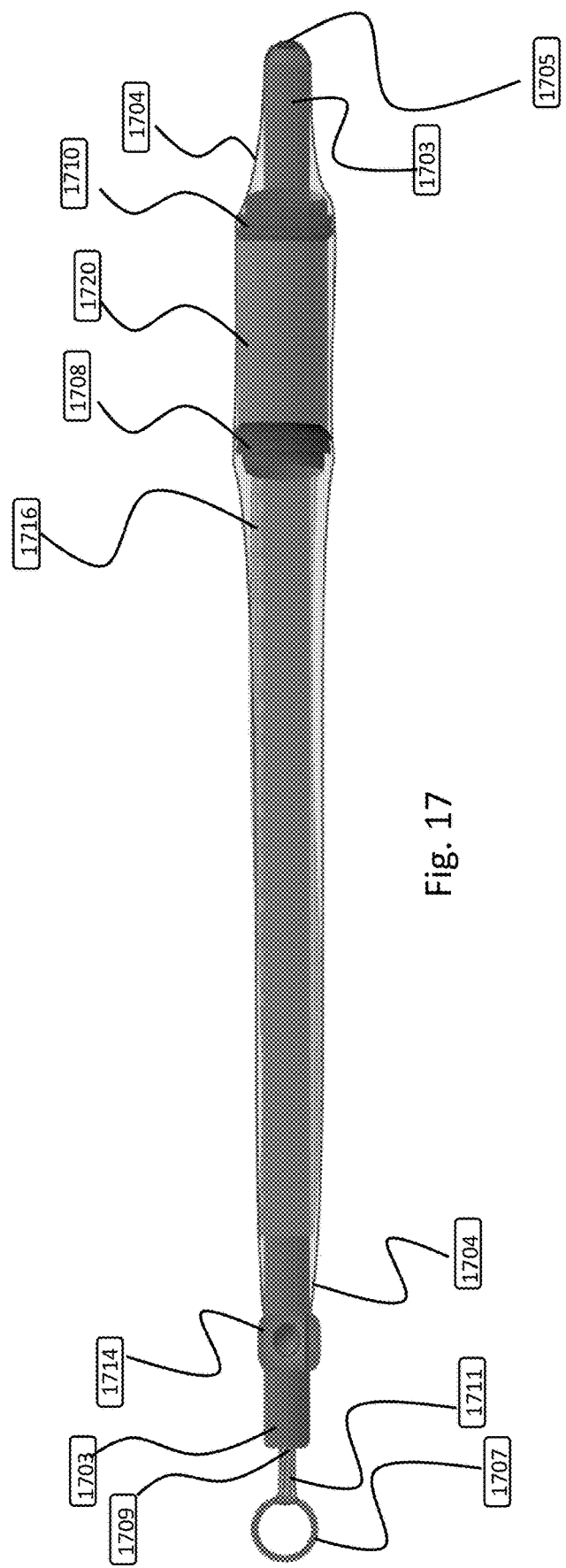
FIG. 17 shows a side view of the anchoring system within a delivery system that includes a flexible membrane and semi-rigid tube pusher.

As shown in FIG. 17, in some embodiments, the delivery system is comprised of a flexible tubular membrane 1704 that wraps around the anchoring system and invaginates down a semi-rigid tube pusher 1703. The flexible tubular membrane 1704 encases the anchoring system and invaginates down the opening 1705 in the proximal end of the semi-rigid tube pusher 1703 and out the distal end of the semi-rigid tube pusher 1703. In some embodiments, the end 1709 of the flexible tubular membrane 1704 on the outside of the semi-rigid tube pusher 1703 is attached with a clamping mechanism 1714 to the semi-rigid tube pusher 1703. The end 1711 of the flexible tubular membrane 1704 that exits out the distal end of the semi-rigid tube pusher 1703 in some embodiments is attached to a handle 1707. Longitudinal traction in the distal direction on the handle 1707 or the end 1711 of the flexible tubular membrane 1704 provides compression of the sealing elements 1708, 1710 and foam 1720. Alternatively, in some embodiments, the end of the flexible tubular membrane 1704 that exits from within the distal end of the semi-rigid tube pusher 1703 is fixed to the end of the semi-rigid tube pusher 1703. Longitudinal traction in the distal direction on the flexible tubular membrane end 1709 outside of the semi-rigid tube pusher 1703 provides compression of the sealing elements and foam to aid in delivery of the device. In these embodiments of the delivery system, the flexible tubular membrane 1704 also holds the semi-rigid tube pusher 1703 to the anchoring system, allowing the anchoring system to be advanced into the bowel with advancement of the semi-rigid tube pusher 1703. Since the flexible tubular membrane 1704 envelops the end of both the anchoring system and the semi-rigid tube pusher 1703, the anchoring system and semi-rigid tube pusher 1703 are held together substantially enough when longitudinal traction is applied to the flexible membrane to allow for advancement of the anchoring system 100 into the colon with advancement of the semi-rigid tube pusher 1703. In some embodiments, the flexible tubular membrane end 1711 that exits the central tube distally is fixed to the semi-rigid tube pusher 1703 so longitudinal traction on only the flexible tubular membrane end 1709 that is on the outside of the semi-rigid tube is required to compress the anchoring system 100 and hold the anchoring system 100 to the semi-rigid tube pusher 1703. In some embodiments, the flexible tubular membrane end that is on the outside of the device 100 and semi-rigid tube pusher 1703 is fixed to the semi-rigid tube pusher 1703 so longitudinal traction on only the flexible tubular membrane end 1711 that exits the distal end of the semi-rigid pusher is required to compress the anchoring system and hold the anchoring system to the semi-rigid tube pusher 1703. Once the device is positioned in place, the flexible tubular membrane 1704 can be detached from the semi-rigid tube pusher 1703 and extracted from the patient's bowels through the center of the semi-rigid tube pusher 1703 by traction on the end 1711 of the flexible tubular membrane that exits the distal end of the semi-rigid tube pusher 1703. The semi-rigid tube pusher 1703 can then be removed from the patient once the anchoring device is activated with negative pressure.

In some embodiments, there is a releasable, fluid-tight, and detachable connector that allows for removal of a length of the sheath outside of the body to allow for more easy delivery of the device. In some embodiments, the connector is located at 8 inches to 36 inches from the closest sealing element. In other embodiments, the sheath is directly connected to the effluence bag or left open at 8 inches to 36 inches from the closest sealing mechanism 110.

According to some embodiments, the device 100 has a removal system that allows it to be removed as needed. Fluid or positive pressure can be delivered down the pressure tube 112 to reduce the adhesive force created to anchor the device 100. The device 100 can then be safely removed from the patient. In some embodiments, the device 100 is configured with a port so that fluid, (ex. Saline solution) can be used to infiltrate tubing in communication with the foam and detach the sleeve 102 from the bowel wall. The fluid can be introduced into the pressure tube 112, or the device 100 can have a separate tube that extends outside the patient's body to provide irrigation. It may be preferable to use the pressure tubing for both negative pressure delivery and irrigation. In some embodiments, the irrigation system is in fluid connection with the pressure tube, wherein the irrigation system introduces a fluid into the pressure tube for irrigation. The irrigation through the tube can be used to wash out abdominal contents that may have leaked around the proximal sealing mechanism 108 and to detach the device 100 from the patient's bowel wall. By use of one or more of these removal methods, the pullout force becomes negligible and the device 100 can be removed without damaging the surrounding tissue.

Other Uses

The embodiments of the invention described herein may have uses outside of protection of damaged bowel or anastomosis protection. For example, the disclosed device and method may also be used for continence control in settings like an Intensive Care Unit. In these settings, fecal contamination of the perineum can result in significant skin irritation and breakdown. Existing continence control devices for diverting fecal flow into a collection bag often result in complications such as fecal leaks, displacement of fecal tubes, and erosion into the bowel wall. In contrast, the device and method described here can anchor a fecal collection sheath within the rectum of a patient with an anchoring mechanism that is non-traumatic, sealed off from leakage, not easily dislodged, and easily reversible. The anchoring methods described herein may also be used to fixate other sheaths or drug delivery devices within the bowel. For example, sheaths for limiting absorption used for treating metabolic disorders, diabetes, or obesity may be anchored using the described technique. Specialized sheaths designed to elute drugs may also be anchored using the described technique. For example, a sheath attached to the anchor device described herein can contain controlled release anti-inflammatory drugs to treat inflammatory bowel disease. Moreover, as described above and shown in FIGS. 18 and 19, a second anchor element can be placed distally to create a sealed space between the treated segment of bowel, the two anchor elements, and the sheath. This space can be filled with therapeutic solutions such as antibiotics, anti-inflammatory drugs, or chemotherapeutic agents for cancer. This allows for controlled local delivery to a segment of bowel wall isolated between the two anchor elements. Also as previously mentioned, sheaths may be anchored that may help with diverting flow from a damaged segment of bowel such as a perforation within the bowel, ischemic bowel, bowel contused by blunt trauma, or bowel that is inflamed or dilated such as in cases of inflammatory bowel disease.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A negative pressure anchor for a body lumen that has a flow there through, a damaged tissue site and an undamaged tissue site apart from the damaged tissue site, the negative pressure anchor comprising:

a sleeve having a sleeve lumen extending though the sleeve with openings on each end allowing the flow of the body lumen to pass through, the sleeve includes an inner side facing the sleeve lumen and an outer side configured to contact the undamaged tissue site, and one end of the sleeve is configured to attach to a sheath and be in sealed fluid communication with the sheath, such that an end of the sheath extends distal to the one end of the sleeve and extends beyond the damaged tissue site in order to cover and protect the damaged tissue site from content flowing through the sheath and the sleeve and thereby allow the flow of the body lumen to pass through the sleeve and the sheath without contacting the undamaged tissue site and the damaged tissue site; and a negative pressure tube coupled to the sleeve and coupled to a negative pressure source, the negative pressure tube is configured to create a negative pressure seal between the outer side of the sleeve and the undamaged tissue site, while allowing the flow of the body lumen to pass through the sleeve, wherein the sleeve is compressible by normal peristaltic forces of a patient's bowel.

2. The negative pressure anchor of claim 1, further comprising a first annular sealing mechanism disposed on a first end of the sleeve and a second annular sealing mechanism disposed on a second end of the sleeve.

3. The negative pressure anchor of claim 2, wherein the first and second annular sealing mechanisms form a substantially airtight and fluid-tight seal with the undamaged tissue site of the body lumen.

4. The negative pressure anchor of claim 2, wherein the first and second annular sealing mechanisms comprise one or more tapered fins placed in series on each end of the sleeve with an orientation directed away from a center of the sleeve so that the one or more tapered fins lie flat against the undamaged tissue site when negative pressure is delivered through the negative pressure tube.

5. The negative pressure anchor of claim 2, wherein the first and second annular sealing mechanisms comprise a rounded protrusion or multiple protrusions placed in series that are compressible.

6. The negative pressure anchor of claim 2, wherein a diameter of each of the first annular sealing mechanism and the second annular sealing mechanism is less than or equal to a diameter of the body lumen at the undamaged tissue site.

7. The negative pressure anchor of claim 2, further comprising a connector tube coupling the negative pressure tube to the sleeve, the connector tube extending through one of the first annular sealing mechanism and the second annular sealing mechanism and having an opening on the outer side of the sleeve.

8. The negative pressure anchor of claim 7, wherein the connector tube includes a one-way valve therein.

9. The negative pressure anchor according to claim 1, wherein the sleeve lumen has a diameter between approximately 1 cm and approximately 6 cm.

10. The negative pressure anchor according to claim 1, wherein the outer side of the sleeve has a diameter between approximately 1.1 cm and approximately 6.1 cm.

11. The negative pressure anchor according to claim 1, wherein the sleeve comprises a flexible material having a Shore A hardness between about 20 A and about 70 A.

12. The negative pressure anchor according to claim 2, wherein the first and second annular sealing mechanisms comprise a flexible material having a Shore A hardness between about 20 A and about 70 A.

13. The negative pressure anchor according to claim 1, further comprising the negative pressure source, wherein negative pressure is applied to the negative pressure tube by the negative pressure source to maintain constant negative pressure at a level between −50 mmHg and −200 mmHg.

14. The negative pressure anchor according to claim 1, wherein the sheath has a length that allows it to extend outside the body lumen.

15. The negative pressure anchor according to claim 1, wherein the sleeve has a length that is between about 3 cm and about 25 cm.

16. The negative pressure anchor according to claim 2, wherein the sleeve, first and second annular sealing mechanisms, and sheath are comprised of one or more of silicone, polyurethane, thermoplastic elastomer, rubber, rubber-like material, or other polymer.

17. The negative pressure anchor according to claim 1, further comprising a plurality of negative pressure tubes in fluid connection with the outer side of the sleeve.

18. The negative pressure anchor according to claim 1, further comprising a surface material disposed on the outer side of the sleeve,
wherein the surface material is a stacked mesh matrix, a honey-comb lattice of interconnected channels oriented in a radial fashion around the sleeve, a gauze, a fabric, a three-dimensional woven material, or open-cell foam.

19. The negative pressure anchor according to claim 2, wherein the sleeve, the first annular sealing mechanism, and the second annular sealing mechanism form a first anchoring element, the negative pressure anchor further comprising:
a second anchoring element in mechanical connection with the sheath, the second anchoring element disposed apart from and distal to the first anchoring element; and
a port disposed between the first anchoring element and the second anchoring element,
wherein the sheath, the first anchoring element, and the second anchoring element create a sealed off space between the first and second anchoring elements, the sheath, and the damaged tissue site, and
wherein the port is in communication with the sealed off space to allow access from outside the patient's bowel for fluid delivery and withdrawal.

20. A delivery system, comprising:
a flexible tubular membrane that encases the negative pressure anchor according to claim 1; and
a semi-rigid tube pusher with a proximal end, a distal end, and a center,
wherein the negative pressure anchor is configured to be pushed into position by advancing the semi-rigid tube pusher into the patient's bowel; and
wherein the flexible tubular membrane invaginates down the proximal end and out the distal end of the semi-rigid tube pusher.

21. The delivery system according to claim 20, wherein the delivery system compresses the negative pressure anchor and holds the negative pressure anchor to the semi-rigid tube pusher when longitudinal traction is applied to the flexible tubular membrane.

22. The delivery system according to claim 21, further comprising a flexible member that can be detached from the semi-rigid tube pusher and extracted from a patient's body through the center of the semi-rigid tube pusher after placement of the negative pressure anchor.

23. A method for anchoring a sheath in a body lumen that has a flow there through, a damaged tissue site and an undamaged tissue site apart from the damaged tissue site, the sheath being in connection with a sleeve and extending distal to the sleeve, the sleeve having a sleeve lumen extending though the sleeve with openings on each end allowing the flow of the body lumen to pass through, the sleeve including an inner side facing the sleeve lumen and an outer side configured to contact the undamaged tissue site, and one end of the sleeve is configured to attach to the sheath and be in sealed fluid communication with the sheath, such that an end of the sheath extends distal to the one end of the sleeve and extends beyond the damaged tissue site allowing the flow of the body lumen to pass through the sleeve and the sheath without contacting the undamaged tissue site and the damaged tissue site, the method comprising:
inserting the sleeve in the body lumen, such that the sleeve is proximal to the damaged tissue site and the sheath covers and protects the damaged tissue site from content flowing through the sheath and the sleeve; and
applying a negative pressure to a region between the outer side of the sleeve and the undamaged tissue site of the body lumen to create a negative pressure seal between the outer side of the sleeve and the undamaged tissue site, while allowing the flow of the body lumen to pass through the sleeve,
wherein the sleeve is compressible by normal peristaltic forces of a patient's bowel.

24. An anchoring system, comprising:
a sleeve having an inner surface defining a first lumen, wherein the sleeve is configured to be disposed in a tissue cavity proximal to a damaged area of tissue of the tissue cavity;
a first annular sealing mechanism disposed at a proximal end of the sleeve;
a second annular sealing mechanism disposed at a distal end of the sleeve;
a pressure tube in fluid connection with an outer surface of the sleeve; and
a sheath in connection with the sleeve, the sheath forming a second lumen, the second lumen being in fluid connection with the first lumen of the sleeve, the sheath having an end in sealed fluid communication with, and extending distal to, a distal end of the sleeve and the second annular sealing mechanism, wherein the end of the sheath, extending distal to the distal end of the sleeve, is configured to cover and protect the damaged area of the tissue of the tissue cavity from content flowing through the second lumen of the sheath and the first lumen of the sleeve;
wherein the anchoring system is configured to apply negative pressure by an external negative pressure source to the pressure tube to form a sealed configuration of the sleeve that substantially prevents displacement of the sleeve in an axial direction due to friction forces between (i) the outer surface of the sleeve and the first and second annular sealing mechanisms of the sleeve; and (ii) the tissue of the tissue cavity proximal to and at a different location from the damaged area of the tissue of the tissue cavity, and wherein the sleeve, the first annular sealing mechanism, and the second annular sealing mechanism are compressible by normal peristaltic forces of a patient's bowel.

* * * * *